(12) United States Patent
Langdale et al.

(10) Patent No.: US 11,259,848 B2
(45) Date of Patent: Mar. 1, 2022

(54) PROXIMAL HUMERAL STABILIZATION SYSTEMS AND METHODS THEREOF

(71) Applicant: GLOBUS MEDICAL, INC., Audubon, PA (US)

(72) Inventors: Evan Langdale, Philadelphia, PA (US); Stephanie Wolfe, Hatfield, PA (US); Peter Evans, Lafayette Hill, PA (US); Barclay Davis, Glenmoore, PA (US)

(73) Assignee: Globus Medical, Inc., Audubon, PA (US)

( * ) Notice: Subject to any disclaimer, the term of this patent is extended or adjusted under 35 U.S.C. 154(b) by 106 days.

(21) Appl. No.: 16/655,572

(22) Filed: Oct. 17, 2019

(65) Prior Publication Data
US 2020/0253648 A1 Aug. 13, 2020

Related U.S. Application Data

(63) Continuation-in-part of application No. 16/274,629, filed on Feb. 13, 2019.

(51) Int. Cl.
| | |
|---|---|
| *A61B 17/72* | (2006.01) |
| *A61B 17/17* | (2006.01) |
| *A61B 17/74* | (2006.01) |
| *A61B 17/80* | (2006.01) |
| *A61F 2/28* | (2006.01) |
| *A61B 17/00* | (2006.01) |

(52) U.S. Cl.
CPC ...... *A61B 17/7283* (2013.01); *A61B 17/7241* (2013.01); *A61B 17/8052* (2013.01); *A61B 17/1717* (2013.01); *A61B 17/1739* (2013.01); *A61B 17/744* (2013.01); *A61B 17/8061* (2013.01); *A61B 2017/00995* (2013.01); *A61F 2002/2853* (2013.01)

(58) Field of Classification Search
CPC .. A61B 17/72–7291; A61B 17/74–748; A61B 17/1717; A61B 2017/00995
See application file for complete search history.

(56) References Cited

U.S. PATENT DOCUMENTS

| | | | |
|---|---|---|---|
| 1,105,105 | A | 7/1914 | Sherman |
| 2,486,303 | A | 10/1949 | Longfellow |
| 3,463,148 | A | 8/1969 | Treace |
| 3,695,259 | A | 10/1972 | Yost |
| 3,716,050 | A | 2/1973 | Johnston |
| 4,119,092 | A | 10/1978 | Gil |

(Continued)

FOREIGN PATENT DOCUMENTS

| | | |
|---|---|---|
| CN | 201987653 U | 9/2011 |
| CN | 202313691 U | 7/2012 |

(Continued)

*Primary Examiner* — Nicholas J Plionis

(57) ABSTRACT

An intramedullary nail implant for positioning in a bone having a head and a shaft defining an intramedullary canal. The implant includes a distal portion having a shaft extending along a central axis and configured for positioning within the intramedullary canal. A proximal portion extends proximally from the distal portion. The proximal portion defines a contact surface which extends at least in part medially of the central axis such that it is configured to extend within a medial portion of the bone head. A method of implanting the nail is also provided.

9 Claims, 32 Drawing Sheets

(56) References Cited

U.S. PATENT DOCUMENTS

| | | |
|---|---|---|
| 4,175,555 A | 11/1979 | Herbert |
| 4,219,015 A | 8/1980 | Steinemann |
| 4,281,649 A | 8/1981 | Derwedunen |
| 4,493,317 A | 1/1985 | Klaue |
| 4,524,765 A | 6/1985 | de Zbikowski |
| 4,651,724 A | 3/1987 | Berentey et al. |
| 4,683,878 A | 8/1987 | Carter |
| 4,781,183 A | 11/1988 | Casey et al. |
| 4,867,144 A | 9/1989 | Karas et al. |
| 4,923,471 A | 5/1990 | Morgan |
| 4,928,679 A * | 5/1990 | Chagneau ......... A61B 17/7283 606/62 |
| 4,966,599 A | 10/1990 | Pollock |
| 5,002,544 A | 3/1991 | Klaue et al. |
| 5,041,114 A | 8/1991 | Chapman et al. |
| 5,151,103 A | 9/1992 | Tepic et al. |
| 5,259,398 A | 11/1993 | Vrespa |
| 5,364,399 A | 11/1994 | Lowery et al. |
| 5,372,598 A | 12/1994 | Luhr et al. |
| 5,375,956 A | 12/1994 | Pennig |
| 5,423,826 A | 6/1995 | Coates et al. |
| 5,468,242 A | 11/1995 | Reisberg |
| D365,634 S | 12/1995 | Morgan |
| 5,489,305 A | 2/1996 | Morgan |
| 5,527,311 A | 6/1996 | Procter et al. |
| 5,536,127 A | 7/1996 | Pennig |
| 5,578,036 A | 11/1996 | Stone et al. |
| 5,601,553 A | 2/1997 | Trebing et al. |
| 5,643,258 A | 7/1997 | Robioneck et al. |
| 5,676,667 A | 10/1997 | Hausman |
| 5,690,631 A | 11/1997 | Duncan et al. |
| 5,709,686 A | 1/1998 | Talos et al. |
| 5,709,687 A | 1/1998 | Pennig |
| 5,718,704 A | 2/1998 | Medoff |
| 5,718,705 A | 2/1998 | Sammarco |
| 5,746,742 A | 5/1998 | Runciman et al. |
| 5,766,175 A | 6/1998 | Martinotti |
| 5,766,176 A | 6/1998 | Duncan |
| 5,779,706 A | 7/1998 | Tschakaloff |
| 5,785,712 A | 7/1998 | Runciman et al. |
| 5,797,914 A | 8/1998 | Leibinger |
| 5,814,048 A | 9/1998 | Morgan |
| 5,925,048 A | 7/1999 | Ahmad et al. |
| 5,938,664 A | 8/1999 | Winquist et al. |
| 5,961,519 A | 10/1999 | Bruce et al. |
| 5,980,540 A | 11/1999 | Bruce |
| 6,001,099 A | 12/1999 | Huebner |
| 6,071,291 A | 6/2000 | Forst et al. |
| 6,093,201 A | 7/2000 | Cooper et al. |
| 6,096,040 A | 8/2000 | Esser |
| 6,107,718 A | 8/2000 | Schustek et al. |
| 6,152,927 A | 11/2000 | Farris et al. |
| 6,206,881 B1 | 3/2001 | Frigg et al. |
| 6,283,969 B1 | 9/2001 | Grusin et al. |
| 6,309,393 B1 | 10/2001 | Tepic et al. |
| 6,322,562 B1 | 11/2001 | Wolter |
| 6,355,043 B1 | 3/2002 | Adam |
| 6,364,882 B1 | 4/2002 | Orbay |
| D458,683 S | 6/2002 | Bryant et al. |
| D458,684 S | 6/2002 | Bryant et al. |
| 6,533,786 B1 | 3/2003 | Needham et al. |
| D479,331 S | 9/2003 | Pike et al. |
| 6,623,486 B1 | 9/2003 | Weaver et al. |
| 6,669,700 B1 | 12/2003 | Farris et al. |
| 6,669,701 B2 | 12/2003 | Steiner et al. |
| 6,712,820 B2 | 3/2004 | Orbay |
| 6,719,759 B2 | 4/2004 | Wagner et al. |
| 6,730,091 B1 | 5/2004 | Pfefferle et al. |
| 6,866,665 B2 | 3/2005 | Orbay |
| 6,955,677 B2 | 10/2005 | Dahners |
| 6,974,461 B1 | 12/2005 | Wolter |
| 7,001,387 B2 | 2/2006 | Farris et al. |
| 7,063,701 B2 | 6/2006 | Michelson |
| 7,090,676 B2 | 8/2006 | Huebner et al. |
| 7,128,744 B2 | 10/2006 | Weaver et al. |
| 7,137,987 B2 | 11/2006 | Patterson et al. |
| 7,153,309 B2 | 12/2006 | Huebner et al. |
| 7,179,260 B2 | 2/2007 | Gerlach et al. |
| 7,250,053 B2 | 7/2007 | Orbay |
| 7,294,130 B2 | 11/2007 | Orbay |
| 7,322,983 B2 | 1/2008 | Harris |
| 7,341,589 B2 | 3/2008 | Weaver et al. |
| 7,344,538 B2 | 3/2008 | Myerson et al. |
| 7,354,441 B2 | 4/2008 | Frigg |
| 7,604,657 B2 | 10/2009 | Orbay et al. |
| 7,632,277 B2 | 12/2009 | Woll et al. |
| 7,635,381 B2 | 12/2009 | Orbay |
| 7,637,928 B2 | 12/2009 | Fernandez |
| 7,655,029 B2 | 2/2010 | Niedernberger et al. |
| 7,655,047 B2 | 2/2010 | Swords |
| 7,695,472 B2 | 4/2010 | Young |
| 7,717,946 B2 | 5/2010 | Oepen et al. |
| 7,722,653 B2 | 5/2010 | Young et al. |
| 7,740,648 B2 | 6/2010 | Young et al. |
| D622,853 S | 8/2010 | Raven, III |
| 7,771,457 B2 | 8/2010 | Kay et al. |
| 7,776,076 B2 | 8/2010 | Grady, Jr. et al. |
| 7,857,838 B2 | 12/2010 | Orbay |
| 7,867,260 B2 | 1/2011 | Meyer et al. |
| 7,867,261 B2 | 1/2011 | Sixto, Jr. et al. |
| 7,875,062 B2 | 1/2011 | Lindemann et al. |
| 7,905,910 B2 | 3/2011 | Gerlach et al. |
| 7,909,858 B2 | 3/2011 | Gerlach et al. |
| 7,951,178 B2 | 5/2011 | Jensen |
| 7,951,179 B2 | 5/2011 | Matityahu |
| 7,976,570 B2 | 7/2011 | Wagner et al. |
| D643,121 S | 8/2011 | Millford et al. |
| D646,785 S | 10/2011 | Milford |
| 8,043,297 B2 | 10/2011 | Grady, Jr. et al. |
| 8,057,520 B2 | 11/2011 | Ducharme et al. |
| 8,062,296 B2 | 11/2011 | Orbay et al. |
| 8,100,953 B2 | 1/2012 | White et al. |
| 8,105,367 B2 | 1/2012 | Austin et al. |
| 8,114,081 B2 | 2/2012 | Kohut et al. |
| 8,118,846 B2 | 2/2012 | Leither et al. |
| 8,118,848 B2 | 2/2012 | Ducharme et al. |
| 8,162,950 B2 | 4/2012 | Digeser et al. |
| 8,167,918 B2 | 5/2012 | Strnad et al. |
| 8,177,820 B2 | 5/2012 | Anapliotis et al. |
| 8,246,661 B2 | 8/2012 | Beutter et al. |
| 8,252,032 B2 | 8/2012 | White et al. |
| 8,257,403 B2 | 9/2012 | Den Hartog et al. |
| 8,257,405 B2 | 9/2012 | Haidukewych et al. |
| 8,257,406 B2 | 9/2012 | Kay et al. |
| 8,262,707 B2 | 9/2012 | Huebner et al. |
| 8,267,972 B1 | 9/2012 | Gehlert |
| 8,317,842 B2 | 11/2012 | Graham et al. |
| 8,323,321 B2 | 12/2012 | Gradl |
| 8,337,535 B2 | 12/2012 | White et al. |
| 8,343,155 B2 | 1/2013 | Fisher et al. |
| 8,382,807 B2 | 2/2013 | Austin et al. |
| 8,394,098 B2 | 3/2013 | Orbay et al. |
| 8,394,130 B2 | 3/2013 | Orbay et al. |
| 8,398,685 B2 | 3/2013 | McGarity et al. |
| 8,403,966 B2 | 3/2013 | Ralph et al. |
| 8,419,775 B2 | 4/2013 | Orbay et al. |
| 8,435,238 B2 | 5/2013 | Dejardin |
| 8,435,272 B2 | 5/2013 | Dougherty et al. |
| 8,439,918 B2 | 5/2013 | Gelfand |
| 8,444,679 B2 | 5/2013 | Ralph et al. |
| 8,491,593 B2 | 7/2013 | Prien et al. |
| 8,496,694 B2 | 7/2013 | Hashmi et al. |
| 8,506,608 B2 | 8/2013 | Cerynik et al. |
| 8,512,384 B2 | 8/2013 | Beutter et al. |
| 8,512,385 B2 | 8/2013 | White et al. |
| 8,518,090 B2 | 8/2013 | Huebner et al. |
| 8,523,862 B2 | 9/2013 | Murashko, Jr. |
| 8,523,919 B2 | 9/2013 | Huebner et al. |
| 8,523,921 B2 | 9/2013 | Horan et al. |
| 8,540,755 B2 | 9/2013 | Whitmore |
| 8,551,095 B2 | 10/2013 | Fritzinger et al. |
| 8,551,143 B2 | 10/2013 | Norris et al. |
| 8,568,462 B2 | 10/2013 | Sixto, Jr. et al. |
| 8,574,268 B2 | 11/2013 | Chan et al. |

(56) References Cited

U.S. PATENT DOCUMENTS

| | | |
|---|---|---|
| 8,597,334 B2 | 12/2013 | Mocanu |
| 8,603,147 B2 | 12/2013 | Sixto, Jr. et al. |
| 8,617,224 B2 | 12/2013 | Kozak et al. |
| 8,632,574 B2 | 1/2014 | Kortenbach et al. |
| 8,641,741 B2 | 2/2014 | Murashko, Jr. |
| 8,641,744 B2 | 2/2014 | Weaver et al. |
| 8,663,224 B2 | 3/2014 | Overes et al. |
| 8,728,082 B2 | 5/2014 | Fritzinger et al. |
| 8,728,126 B2 | 5/2014 | Steffen |
| 8,740,905 B2 | 6/2014 | Price et al. |
| 8,747,442 B2 | 6/2014 | Orbay et al. |
| 8,764,751 B2 | 7/2014 | Orbay et al. |
| 8,764,808 B2 | 7/2014 | Gonzalez-Hernandez |
| 8,777,998 B2 | 7/2014 | Daniels et al. |
| 8,790,376 B2 | 7/2014 | Fritzinger et al. |
| 8,790,377 B2 | 7/2014 | Ralph et al. |
| 8,808,333 B2 | 8/2014 | Kuster et al. |
| 8,808,334 B2 | 8/2014 | Strnad et al. |
| 8,834,532 B2 | 9/2014 | Velikov et al. |
| 8,834,537 B2 | 9/2014 | Castanada et al. |
| 8,852,246 B2 | 10/2014 | Hansson |
| 8,852,249 B2 | 10/2014 | Ahrens et al. |
| 8,864,802 B2 | 10/2014 | Schwager et al. |
| 8,870,931 B2 | 10/2014 | Dahners et al. |
| 8,888,825 B2 | 11/2014 | Batsch et al. |
| 8,906,076 B2 | 12/2014 | Mocanu et al. |
| 8,911,482 B2 | 12/2014 | Lee et al. |
| 8,926,675 B2 | 1/2015 | Leung et al. |
| 8,940,026 B2 | 1/2015 | Hilse et al. |
| 8,940,028 B2 | 1/2015 | Austin et al. |
| 8,940,029 B2 | 1/2015 | Leung et al. |
| 8,951,291 B2 | 2/2015 | Impellizzeri |
| 8,968,368 B2 | 3/2015 | Tepic |
| 8,968,371 B2 | 3/2015 | Humphrey |
| 9,011,457 B2 | 4/2015 | Grady, Jr. et al. |
| 9,023,052 B2 | 5/2015 | Lietz et al. |
| 9,050,151 B2 | 6/2015 | Schilter |
| 9,072,553 B2 | 7/2015 | Dejardin |
| 9,072,555 B2 | 7/2015 | Michel |
| 9,072,557 B2 | 7/2015 | Fierlbeck et al. |
| 9,107,678 B2 | 8/2015 | Murner et al. |
| 9,107,711 B2 | 8/2015 | Hainard |
| 9,107,713 B2 | 8/2015 | Horan et al. |
| 9,107,718 B2 | 8/2015 | Isch |
| 9,113,970 B2 | 8/2015 | Lewis et al. |
| 9,149,310 B2 | 10/2015 | Fritzinger et al. |
| 9,161,791 B2 | 10/2015 | Frigg |
| 9,161,795 B2 | 10/2015 | Chasbrummel et al. |
| 9,168,075 B2 | 10/2015 | Dell'Oca |
| 9,179,950 B2 | 11/2015 | Zajac et al. |
| 9,179,956 B2 | 11/2015 | Cerynik et al. |
| 9,180,020 B2 | 11/2015 | Gause et al. |
| 9,211,151 B2 | 12/2015 | Weaver et al. |
| 9,259,217 B2 | 2/2016 | Fritzinger et al. |
| 9,259,255 B2 | 2/2016 | Lewis et al. |
| 9,271,769 B2 | 3/2016 | Batsch et al. |
| 9,283,010 B2 | 3/2016 | Medoff et al. |
| 9,295,506 B2 | 3/2016 | Raven, III et al. |
| 9,314,284 B2 | 4/2016 | Chan et al. |
| 9,320,554 B2 | 4/2016 | Greenberg et al. |
| 9,322,562 B2 | 4/2016 | Takayama et al. |
| 9,370,388 B2 | 6/2016 | Globerman et al. |
| D765,851 S | 9/2016 | Early et al. |
| 9,433,407 B2 | 9/2016 | Fritzinger et al. |
| 9,433,452 B2 | 9/2016 | Weiner et al. |
| 9,451,971 B2 | 9/2016 | Warburton et al. |
| 9,452,004 B2 | 9/2016 | Larche et al. |
| 9,468,479 B2 | 10/2016 | Marotta et al. |
| 9,480,512 B2 | 11/2016 | Orbay |
| 9,486,262 B2 | 11/2016 | Andermahr et al. |
| 9,492,213 B2 | 11/2016 | Orbay |
| 9,510,878 B2 | 12/2016 | Nanavati et al. |
| 9,510,880 B2 | 12/2016 | Terrill et al. |
| 9,526,543 B2 | 12/2016 | Castaneda et al. |
| 9,545,277 B2 | 1/2017 | Wolf et al. |
| 9,549,819 B1 | 1/2017 | Bravo et al. |
| 9,566,097 B2 | 2/2017 | Fierlbeck et al. |
| 9,579,133 B2 | 2/2017 | Guthlein |
| 9,622,799 B2 | 4/2017 | Orbay et al. |
| 9,636,157 B2 | 5/2017 | Medoff |
| 9,649,141 B2 | 5/2017 | Raven, III et al. |
| 9,668,794 B2 | 6/2017 | Kuster et al. |
| 9,801,670 B2 | 10/2017 | Hashmi et al. |
| 9,814,504 B2 | 11/2017 | Ducharme et al. |
| 10,111,693 B2 | 10/2018 | Kannen et al. |
| 2002/0045901 A1 | 4/2002 | Wagner et al. |
| 2003/0073999 A1* | 4/2003 | Putnam ............... A61B 17/7291 606/62 |
| 2004/0097937 A1 | 5/2004 | Pike et al. |
| 2005/0107796 A1 | 5/2005 | Gerlach et al. |
| 2005/0131413 A1 | 6/2005 | O'Driscoll et al. |
| 2005/0187551 A1 | 8/2005 | Orbay et al. |
| 2006/0149265 A1 | 7/2006 | James et al. |
| 2006/0241607 A1 | 10/2006 | Myerson et al. |
| 2007/0173840 A1 | 7/2007 | Huebner |
| 2007/0255283 A1* | 11/2007 | Ekholm ................. A61B 17/72 606/64 |
| 2007/0270849 A1 | 11/2007 | Orbay et al. |
| 2007/0288022 A1 | 12/2007 | Lutz |
| 2008/0021477 A1 | 1/2008 | Strnad et al. |
| 2008/0234749 A1 | 9/2008 | Forstein |
| 2008/0275510 A1 | 11/2008 | Schonhardt et al. |
| 2009/0024172 A1 | 1/2009 | Pizzicara |
| 2009/0024173 A1 | 1/2009 | Reis, Jr. |
| 2009/0118773 A1 | 5/2009 | James et al. |
| 2009/0198285 A1 | 8/2009 | Raven, III |
| 2009/0228010 A1 | 9/2009 | Gonzalez-Hernandez et al. |
| 2009/0228047 A1 | 9/2009 | Derouet et al. |
| 2009/0248084 A1 | 10/2009 | Hintermann |
| 2009/0281543 A1 | 11/2009 | Orbay et al. |
| 2009/0299369 A1 | 12/2009 | Orbay et al. |
| 2009/0312760 A1 | 12/2009 | Forstein et al. |
| 2009/0326533 A1 | 12/2009 | Dell'Oca |
| 2010/0057086 A1 | 3/2010 | Price et al. |
| 2010/0114097 A1 | 5/2010 | Siravo et al. |
| 2010/0121326 A1 | 5/2010 | Woll et al. |
| 2010/0274247 A1 | 10/2010 | Grady, Jr. et al. |
| 2011/0106086 A1 | 5/2011 | Laird |
| 2011/0218580 A1 | 9/2011 | Schwager et al. |
| 2012/0010667 A1 | 1/2012 | Eglseder |
| 2012/0059424 A1 | 3/2012 | Epperly et al. |
| 2012/0203227 A1 | 8/2012 | Martin |
| 2012/0232599 A1 | 9/2012 | Schoenly et al. |
| 2012/0323284 A1 | 12/2012 | Baker et al. |
| 2013/0018426 A1 | 1/2013 | Tsai et al. |
| 2013/0046347 A1 | 2/2013 | Cheng et al. |
| 2013/0060291 A1 | 3/2013 | Petersheim |
| 2013/0123841 A1 | 5/2013 | Lyon |
| 2013/0138156 A1 | 5/2013 | Derouet |
| 2013/0150902 A1 | 6/2013 | Leite |
| 2013/0165981 A1 | 6/2013 | Clasbrummet et al. |
| 2013/0211463 A1 | 8/2013 | Mizuno et al. |
| 2013/0289630 A1 | 10/2013 | Fritzinger |
| 2014/0005728 A1 | 1/2014 | Koay et al. |
| 2014/0018862 A1 | 1/2014 | Koay et al. |
| 2014/0031879 A1 | 1/2014 | Sixto, Jr. et al. |
| 2014/0066998 A1 | 3/2014 | Martin |
| 2014/0094856 A1 | 4/2014 | Sinha |
| 2014/0121710 A1 | 5/2014 | Weaver et al. |
| 2014/0180345 A1 | 6/2014 | Chan et al. |
| 2014/0277178 A1 | 9/2014 | O'Kane et al. |
| 2014/0277181 A1 | 9/2014 | Garlock |
| 2014/0316473 A1 | 10/2014 | Pfeffer et al. |
| 2014/0330320 A1 | 11/2014 | Wolter |
| 2014/0378975 A1 | 12/2014 | Castaneda et al. |
| 2015/0051650 A1 | 2/2015 | Verstreken et al. |
| 2015/0051651 A1 | 2/2015 | Terrill et al. |
| 2015/0073486 A1 | 3/2015 | Marotta et al. |
| 2015/0105829 A1 | 4/2015 | Laird |
| 2015/0112355 A1 | 4/2015 | Dahners et al. |
| 2015/0134011 A1 | 5/2015 | Medoff |
| 2015/0142065 A1 | 5/2015 | Schonhardt et al. |
| 2015/0190185 A1 | 7/2015 | Koay et al. |
| 2015/0209091 A1 | 7/2015 | Sixto, Jr. et al. |

(56) References Cited

U.S. PATENT DOCUMENTS

| | | |
|---|---|---|
| 2015/0216571 A1 | 8/2015 | Impellizzeri |
| 2015/0223852 A1 | 8/2015 | Lietz et al. |
| 2015/0272638 A1 | 10/2015 | Langford |
| 2015/0282851 A1 | 10/2015 | Michel |
| 2015/0313653 A1 | 11/2015 | Ponce et al. |
| 2015/0313654 A1 | 11/2015 | Horan et al. |
| 2015/0327898 A1 | 11/2015 | Martin |
| 2015/0351816 A1 | 12/2015 | Lewis et al. |
| 2015/0374421 A1 | 12/2015 | Rocci et al. |
| 2016/0022336 A1 | 1/2016 | Bateman |
| 2016/0030035 A1 | 2/2016 | Zajac et al. |
| 2016/0045237 A1 | 2/2016 | Cerynik et al. |
| 2016/0045238 A1 | 2/2016 | Bohay et al. |
| 2016/0074081 A1 | 3/2016 | Weaver et al. |
| 2016/0166297 A1 | 6/2016 | Mighell et al. |
| 2016/0166298 A1 | 6/2016 | Mighell et al. |
| 2016/0166393 A1 | 6/2016 | Visser et al. |
| 2016/0183990 A1 | 6/2016 | Koizumi et al. |
| 2016/0262814 A1 | 9/2016 | Wainscott |
| 2016/0278828 A1 | 9/2016 | Ragghianti |
| 2016/0310183 A1 | 10/2016 | Shah et al. |
| 2016/0310185 A1 | 10/2016 | Sixto et al. |
| 2016/0324552 A1 | 11/2016 | Baker et al. |
| 2016/0354122 A1 | 12/2016 | Montello et al. |
| 2017/0035478 A1 | 2/2017 | Andermahr et al. |
| 2017/0042592 A1 | 2/2017 | Kim |
| 2017/0042596 A9 | 2/2017 | Mighell et al. |
| 2017/0049493 A1 | 2/2017 | Gauneau et al. |
| 2017/0065312 A1 | 3/2017 | Lauf et al. |
| 2017/0105775 A1 | 4/2017 | Ricker et al. |
| 2017/0215931 A1 | 8/2017 | Cremer et al. |

FOREIGN PATENT DOCUMENTS

| | | | |
|---|---|---|---|
| CN | 202821574 U | | 3/2013 |
| CN | 202821575 U | | 3/2013 |
| CN | 203506858 U | | 4/2014 |
| CN | 203815563 U | | 9/2014 |
| CN | 105982727 A | | 10/2016 |
| CN | 107616830 A | | 1/2018 |
| CN | 108904027 A | * | 11/2018 |
| CN | 108904027 B | | 11/2018 |
| EP | 0639352 A1 | | 2/1995 |
| FR | 2846870 A1 | | 5/2004 |
| FR | 2928259 A1 | | 9/2009 |
| JP | 2003210478 A | | 7/2003 |
| TW | 201316942 A | | 5/2013 |
| WO | 2008129995 A1 | | 10/2008 |
| WO | 2016079504 A1 | | 5/2016 |

\* cited by examiner

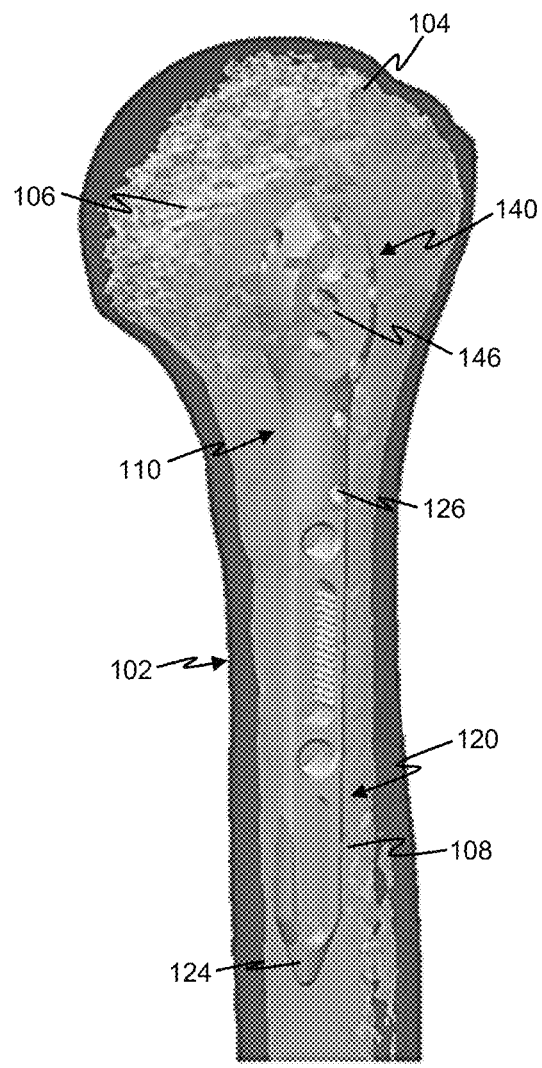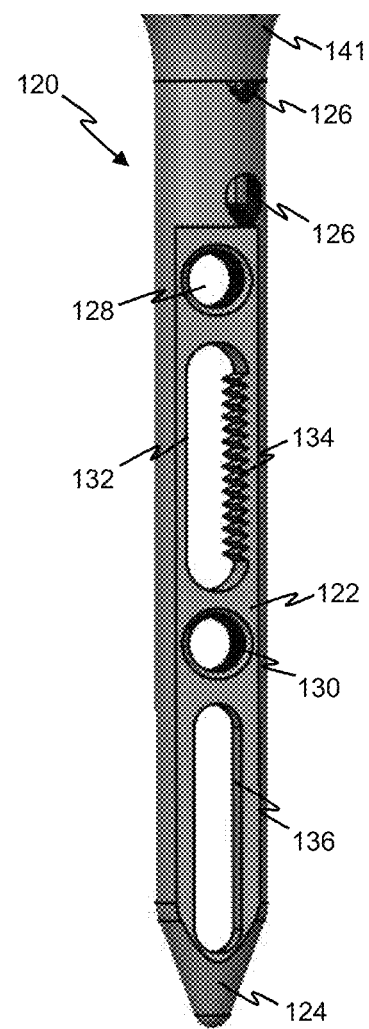
Fig. 1
Fig. 2

PROXIMAL HUMERAL STABILIZATION SYSTEMS AND METHODS THEREOF

CROSS-REFERENCE TO RELATED APPLICATIONS

The present application is a continuation-in-part of U.S. application Ser. No. 16/274,629 filed on Feb. 13, 2019, which is hereby incorporated by reference in its entirety.

FIELD

The present disclosure relates to surgical devices and stabilization systems, for example, for trauma applications, and more particularly, for stabilization of proximal humeral fractures.

BACKGROUND

Bone fractures are often repaired by internal fixation of the bone, such as diaphyseal bone, using one or more plates. The plate is held against the fractured bone with screws, for example, which engage the bone and heads which provide a compressive force against the plate. The plate and bone are thus forced against each other in a manner that transfers load primarily between a bone contacting surface of the plate and the bone surface to reinforce the fractured bone during healing. This manner of plating generally creates relatively low stress concentration in the bone, as there may be a large contact area between the plate and the diaphyseal bone surface permitting transfer of load to be dispersed. There may be a desire to use locking screws, non-locking screws, or a combination of both that are able to dynamically compress the bone. Of course, the designs of the plates, types of screws, and locking and/or non-locking capabilities may vary based on the location and type of fracture.

The three long bones of the upper extremity are the humerus, radius, and ulna. In the case of proximal humerus fracture fixation, plating of the lateral bone surface may be desirable. In some cases, plating alone may lead to humeral head collapse during healing, and the addition of an allograft fibular strut inside of the intramedullary canal and inserted through the fracture site may prevent head collapse. There remains a need, however, for improved intramedullary or calcar systems that provide appropriate stabilization to the humerus.

SUMMARY

To meet this and other needs, devices, systems, and methods of bone stabilization are provided, for example, for humerus stabilization. This includes a bone stabilization construct for positioning in a bone having a head and a shaft defining an intramedullary canal. The construct includes an intramedullary nail implant having a distal portion including a shaft extending along a central axis and configured for positioning within the intramedullary canal, wherein the distal portion defines a slot, and the slot includes a linear rack with a plurality of teeth extending into the slot. The nail also includes a proximal portion extending proximally from the distal portion, the proximal portion defining a contact surface which extends at least in part medially of the central axis and which is configured to extend within the head of the bone. The construct also includes a screw, configured to fill a hole left from a guide used to position the intramedullary nail, the screw comprising a distal end having a smaller diameter than a proximal end of the screw.

Also provided is a bone stabilization construct for positioning in a bone having a head and a shaft defining an intramedullary canal. The construct includes an intramedullary nail implant having a distal portion including a shaft extending along a central axis and configured for positioning within the intramedullary canal, wherein the distal portion defines a slot, and the slot includes a linear rack with a plurality of teeth extending into the slot. The nail also includes a proximal portion extending proximally from the distal portion, the proximal portion defining a contact surface which extends at least in part medially of the central axis and which is configured to extend within the head of the bone. The construct also includes a screw, configured to fill a hole left from a guide used to position the intramedullary nail, the screw comprising a distal end having a smaller diameter than a proximal end of the screw, wherein the screw is threaded at the proximal end and has an unthreaded stud at the distal end.

Also provided are kits for the stabilization systems including bone plates of varying sizes and orientations, intramedullary nails of varying sizes and orientations, fasteners including locking fasteners, non-locking, compression fasteners, polyaxial fasteners, fixed angle fasteners, or any other suitable fasteners, drill guides, k-wires, sutures, and other components for installing the same.

BRIEF DESCRIPTION OF THE DRAWINGS

The accompanying drawings, which are incorporated herein and constitute part of this specification, illustrate the presently preferred embodiments of the disclosure, and, together with the general description given above and the detailed description given below, serve to explain the features of the disclosure. In the drawings:

FIG. 1 is a perspective view of an intramedullary nail positioned in the intramedullary canal of a humerus in accordance with an embodiment of the disclosure.

FIG. 2 is a perspective view of a distal portion of the intramedullary nail of FIG. 1.

DETAILED DESCRIPTION

Figure 3:
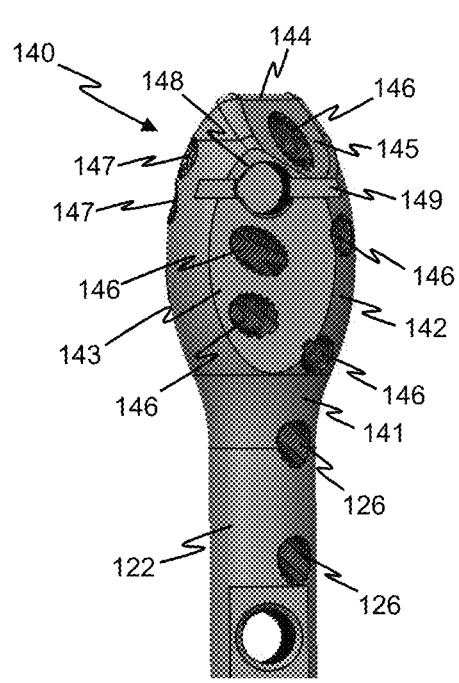
FIG. 3 is a perspective view of a proximal portion of the intramedullary nail of FIG. 1.

In the drawings, like numerals indicate like elements throughout. Certain terminology is used herein for convenience only and is not to be taken as a limitation on the present disclosure. The following describes preferred embodiments of the present disclosure. However, it should be understood, based on this disclosure, that the disclosure is not limited by the preferred embodiments described herein.

The following disclosure uses terms and anatomy specific to proximal humerus fracture fixation, however, it will be appreciated that with changes, such as dimensional changes, the devices can be used in many different locations within the body.

Referring to FIGS. 1-3, an intramedullary nail implant 110 in accordance with an embodiment of the disclosure will be described. The intramedullary nail implant 110 includes a distal portion 120 and a proximal portion 140. The distal portion 120 includes a shaft 122 which fits in the intramedullary canal 108 of the bone 102. The proximal portion 140 is configured to fill the head 104 of the bone 102. The intramedullary implant 110 may be anatomically shaped, for example, with a range of medial bends towards the proximal head for increased support.

The nail 110 may be manufactured, for example, as a one-piece device as illustrated or a modular device to be able to pair two different proximal and distal designs to treat different fractures and anatomies. If two separate components, the distal and proximal portions 120, 140 may be coupled to one another, for example, through a mechanical mechanism. For example, the distal portion 120 may include a male, threaded portion and the proximal portion 140 may include a female, threaded portion configured to receive the male, threaded portion of the distal portion 120 to couple the two parts together. Such a modular configuration may be similar to the designs described with respect to FIGS. 4A-4H of U.S. patent application Ser. No. 15/704,044 (the '044 application). The complete disclosure of the '044 application is incorporated herein by reference in its entirety for all purposes. The proximal and distal portions 140, 120 may be coupled together by any suitable means, such as a dovetail connection, press-fit, threaded, snap-fit, or the like. In other embodiments, it should be noted that the proximal portion 140 and the distal portion 120 can be exchanged and/or interchangeable to facilitate fixation of different fractures and anatomies. Furthermore, each of the intramedullary nails disclosed herein may function as a standalone device or may be compatible with lateral plating in a manner as described in the '044 application.

The proximal and distal portions 140, 120 may each have a width (or diameter) and a length. The width or diameter of the proximal portion 140 may be greater than the width or diameter of the distal portion 120, and the length of the distal portion 120 may be greater than the length of the proximal portion 140. Preferably, the proximal portion 140 is sized and dimensioned to be substantially received within the humeral head 104 and the distal portion 120 is sized and dimensioned to be substantially received within the intramedullary canal 108.

Referring to FIGS. 1 and 2, the distal portion 120 is configured as an elongate shaft or stem. The distal portion 120 of the implant 110 may be a single body that extends from the junction 141 with proximal portion 140 towards the distal portion of the humerus 102. The distal portion 120 may be configured as a cylindrical shaft, however, the shaft may be configured as any geometrical shape (e.g., rectangular, oblong, polygonal, or the like) that suits the intramedullary canal 108. The shaft or distal portion 120 may be compatible with reverse or hemi shoulder arthroplasty implants.

The distal portion 120 forms a body 122 extending to a distal tip 124 and having a plurality of through openings or holes 126 for receiving fasteners 160 as described herein. Each of the plurality of holes 126 of the distal portion 120 may have an entry point and an exit point. The holes 126 may be threaded or textured (e.g., to receive locking fasteners 160) or non-threaded/non-textured (e.g., to receive compression fasteners). The holes 126 in the distal portion 120 may be conical, for example, to accept polyaxial screws. The distal portion 120 may further define one or more holes 128, 130 configured to receive alignment/stability posts, as will be described hereinafter. The distal portion 120 can also be cemented or press fit in to the canal 108 based on surgeon preference.

In the present embodiment, the distal portion 120 further defines a pair of slots 132, 136 extending through the body 122. One of the slots 132 has a plurality of teeth which define a rack 132. The rack 134 may be a linear rack extending in the proximal-distal direction. The rack 134 may extend along a length of the slot 132, for example, substantially along one or both sides of the slot 132. The teeth of the rack 134 may extend inwardly into the slot opening. The rack 134 is configured to be engaged by a pinion of external instrument. Such engagement allows proximal or distal movement of the nail 110 which may aid in the reduction, expansion, and/or manipulation of the fracture, as described in detail below. It is also envisioned that the rack 134 may be curved or otherwise configured to engage with the pinion. The teeth of the rack 134 may also be designed to provide bi-directional or uni-directional movement.

The distal portion 120 may have an optional hydroxyapatite (HA) coating, smooth or porous coatings. According to another embodiment, the distal portion 120 may be configured to have mesh type surface, similar or different from the mesh of the proximal portion 140' described below. The device will be available in a range of lengths and diameters. According to yet another embodiment, the distal portion 120 may also be made with an expandable diameter to give surgeons greater flexibility in sizing and also facilitate distal locking, reducing typical complications. Reaming may not be necessary before implant insertion.

Referring to FIGS. 1 and 3, the proximal portion 140 of the intramedullary nail 110 will be described. It should be noted that the proximal portion 140 may be any geometrical shape that best suits the positioning of the implant 110 within the humeral head 104. For instance, the proximal portion 140 may be rectangular, oblong, polygonal, or the like. In the present embodiment, the proximal portion 140 includes a body 142 having an oval shape extending from the junction 141 with the distal portion 120 to a proximal end 144. The oval shape provides a curved surface which extends medially of a central axis of the shaft 122 such that it extends into and supports the medial portion of the humeral head 104. In the present embodiment, the body 142 is formed as a solid structure with a plurality of through openings or holes 146 for receiving the fasteners 160 described herein. While a solid body 142 is illustrated, it is also contemplated that the proximal portion 140 may be configured having a hollow body with the plurality of holes 146 on the exterior surface of the cylinder and extending through the width or diameter of the cylinder.

The holes 146 may be positioned on the proximal portion 140 so that the fasteners 160 enter the holes and rigidly couple the proximal portion 140 to bone and/or bone fragments of the humeral head 104, including the cortical wall 106. Each of the plurality of holes 146 of the proximal portion 140 may have an entry point and an exit point 147. The holes 146 may be threaded or textured (e.g., to receive locking fasteners 160) or non-threaded/non-textured (e.g., to receive compression fasteners). Holes 146 can also have a bushing or insert to accept the screw and lock the screw either at the bone thread of the screw or the head of the screw. Flattened regions 143, 145 may be defined about one or more of the holes 146 to facilitate bone engagement. In addition to the screw holes 146, the proximal portion 140 includes a guide mounting blind bore 148 and slot 149, which will be described in more detail hereinafter.

Figure 4:
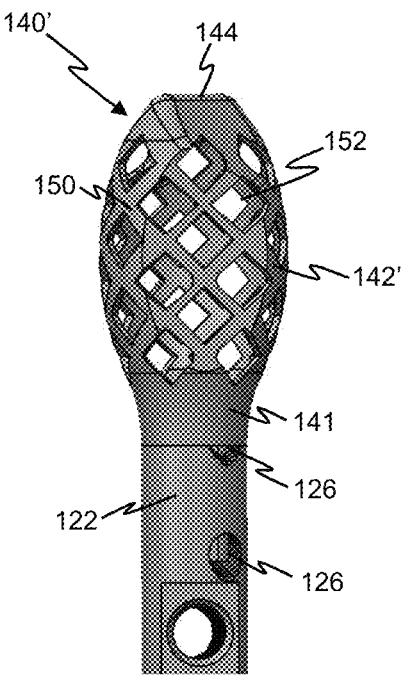
FIG. 4 is a perspective view illustrating a proximal portion of an intramedullary nail in accordance with another embodiment of the disclosure.
Figure 5:
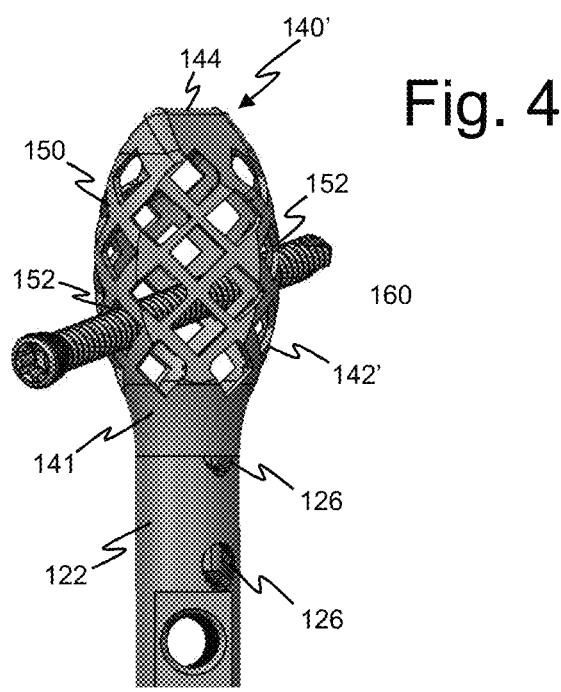
FIG. 5 is a perspective view illustrating a screw extending through the proximal portion of FIG. 4.

Referring to FIGS. 4 and 5, a proximal portion 140' in accordance with another embodiment of the disclosure will be described. In this embodiment, the proximal portion 140' includes a body 142' defined by a mesh or mesh-like surface 150. The cage or proximal portion 140 may have a coarser mesh 150 which defines holes 152 having a diameter larger than the diameter of the screws 160 to allow the screws to be passed through the mesh body 142' to lock the proximal portion 140' in place. In one embodiment, the holes 152 may be non-circular in shape. For example, the holes 152 may be generally square or rectangular in cross-section. In some embodiments, the holes 152 may have one or more planar surfaces (e.g., up to four planar surfaces) forming the outer perimeter of the holes 152. The holes 152 may be the same size or smaller than the diameter of the screws 160 and the mesh-like body 142' may be configured to deform to accommodate the screws 160. The mesh-like body 142' may be substantially rigid or may have some flexibility. The body 142' can be made from typical implant materials such as stainless steel or titanium, but may also be made of less common materials such as nitinol, which has the ability to flex out of the way of screws without breaking the screw or body 142'. Bone graft or other biological/bioactive material can be injected into the proximal portion 140' if desired.

Figure 6:
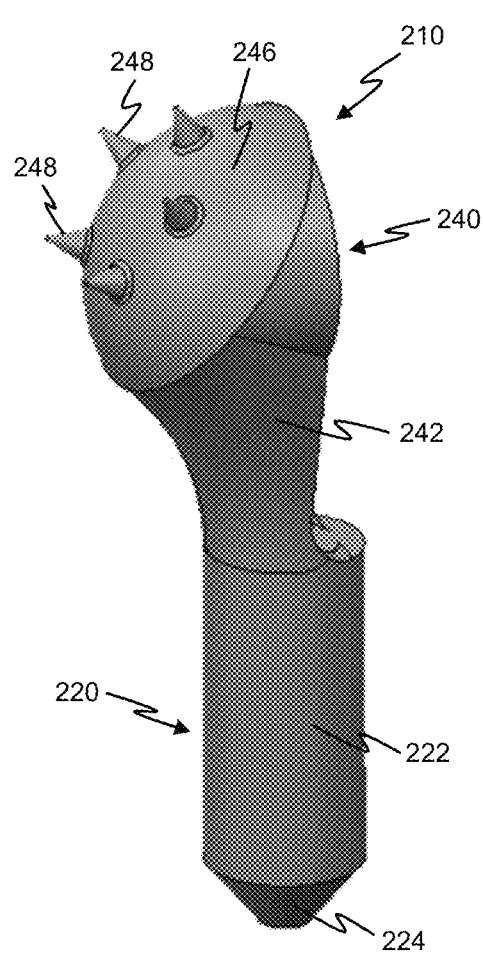
FIGS. 6 and 7 are front and rear perspective views, respectively, of an intramedullary nail in accordance with another embodiment of the disclosure.
Figure 7:
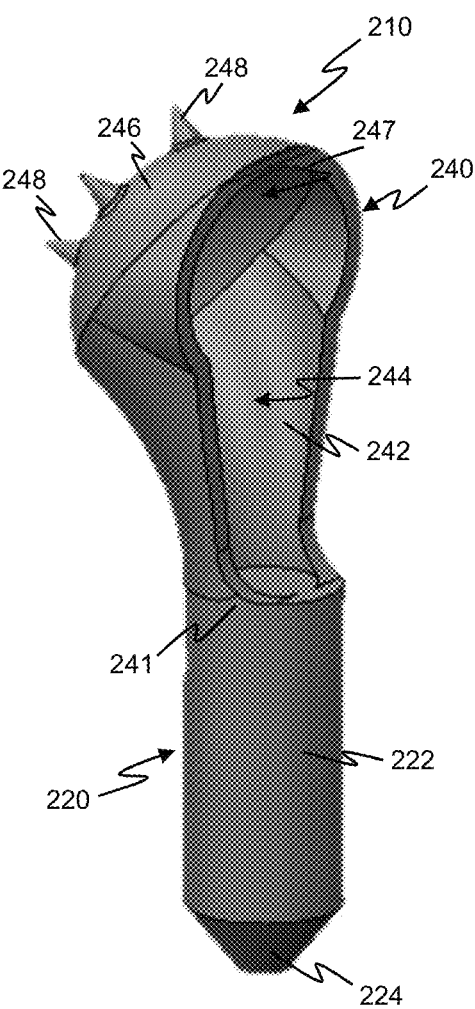

Referring to FIGS. 6 and 7, an intramedullary nail implant 210 in accordance with another embodiment of the disclosure will be described. The implant 210 includes a distal portion 220 and a proximal portion 240. The distal portion 220 is again configured as an elongate shaft or stem which extends from the junction 241 with proximal portion 240 towards the distal portion of the humerus 102. The distal portion 220 may be configured as a cylindrical shaft, however, the shaft may be configured as any geometrical shape (e.g., rectangular, oblong, polygonal, or the like) that suits the intramedullary canal 108. The distal portion 220 forms a body 222 extending to a distal tip 224. In the illustrated embodiment, the distal portion body 222 is a solid structure without holes. With this configuration, the body 222 is preferably manufactured from a material which is penetrable by screws or the like to lock the distal portion in place (see FIG. 9). Alternatively, the body 242 may have a hollow configuration with screws passing through one wall and into the hollow area. The screws may further extend through the opposite wall. As another alternative, the body 422 may have defined screw holes or slots. The distal portion 220 can also be cemented or press fit in to the canal 108 based on surgeon preference.

The proximal portion 240 of the implant 210 includes a body 242 defined by a semi-circumferential wall 250 which extends from the junction 241 to a domed proximal end 246. The domed proximal end 246 provides a curved surface which extends medially of a central axis of the shaft 222 such that it extends into and supports the medial portion of the humeral head 104. As shown in FIG. 7, the wall 250 defines a hollow cavity 244 and the domed proximal end 246 defines a hollow cavity 247. With this configuration, the proximal portion 240 is defined by a thin material and either screws 160 or k-wires (not shown) may be passed through the bone and the nail 210. A screw can be passed after pre-drilling through the bone and nail. A softer material may be useful in this application, included but not limiting to polyether ether ketone (PEEK), polylactic acid, or the like. A series of sharp protuberances 248 extend from the domed proximal end 246 to retain the head 104 onto the nail 210. Similar protuberances may be provided on any of the nails described herein.

Figure 8:
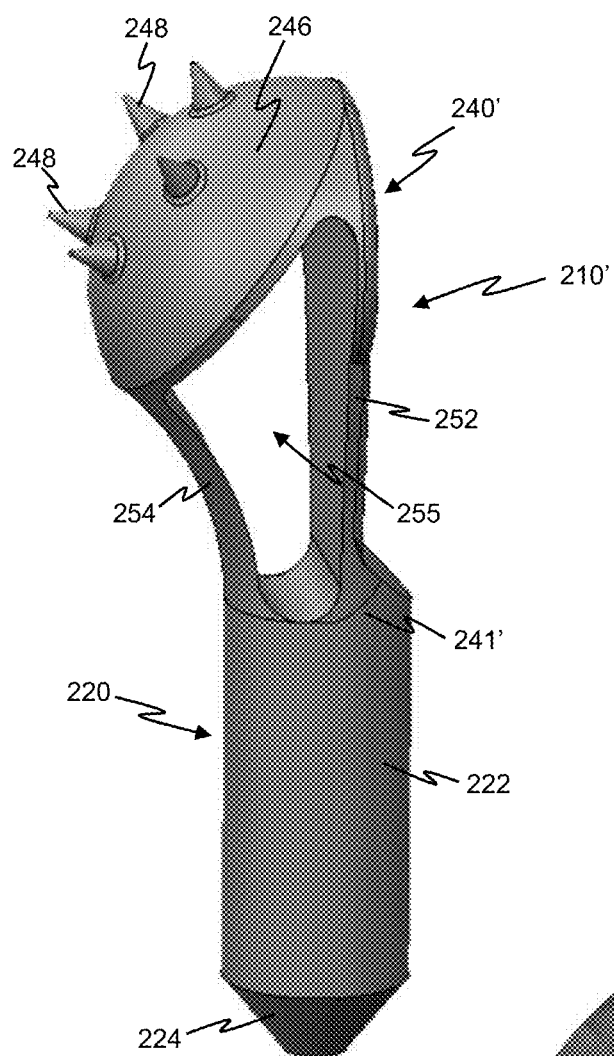
FIG. 8 is a perspective view of an intramedullary nail in accordance with another embodiment of the disclosure.
Figure 9:
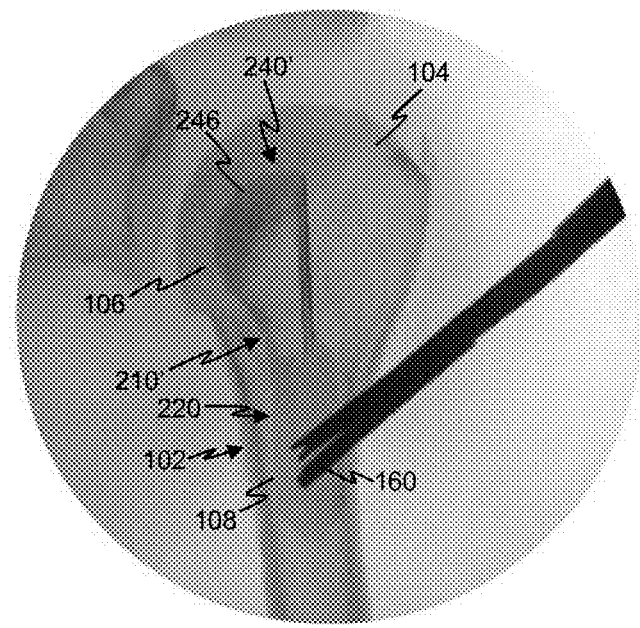
FIG. 9 is an x-ray image showing the intramedullary nail of FIG. 8 positioned in the intramedullary canal of a humerus.

Referring to FIGS. 8 and 9, another intramedullary nail implant 210' in accordance with an embodiment of the disclosure will be described. The implant 210' is substantially the same as in the previous embodiment and only differences will be described. In the present embodiment, the body of the proximal portion 240' is defined by a pair of opposed walls 252, 254 with an open space 255 therebetween. The walls 252, 254 extend from the junction 241' to the domed proximal end 246. The open space 255 allows for a greater variability of freehand hole trajectories.

In embodiments illustrated in FIGS. 6-9, it is noted that the distal and proximal portions are designed with a degree of eccentricity so that when the distal portion 220 is rotated in the canal 108, the proximal portion 240, 240' with a larger diameter will act as a cam pushing the humeral head 104 medially into position. Further shapes may include anatomically contoured devices with a range of medial bends for increased support of the proximal head, or lateral bends for greater tuberosity support. There may be accommodations for suture fixation on the top of the head. Large holes will be placed to accommodate a wide variety of suture size and shapes.

Figure 10:
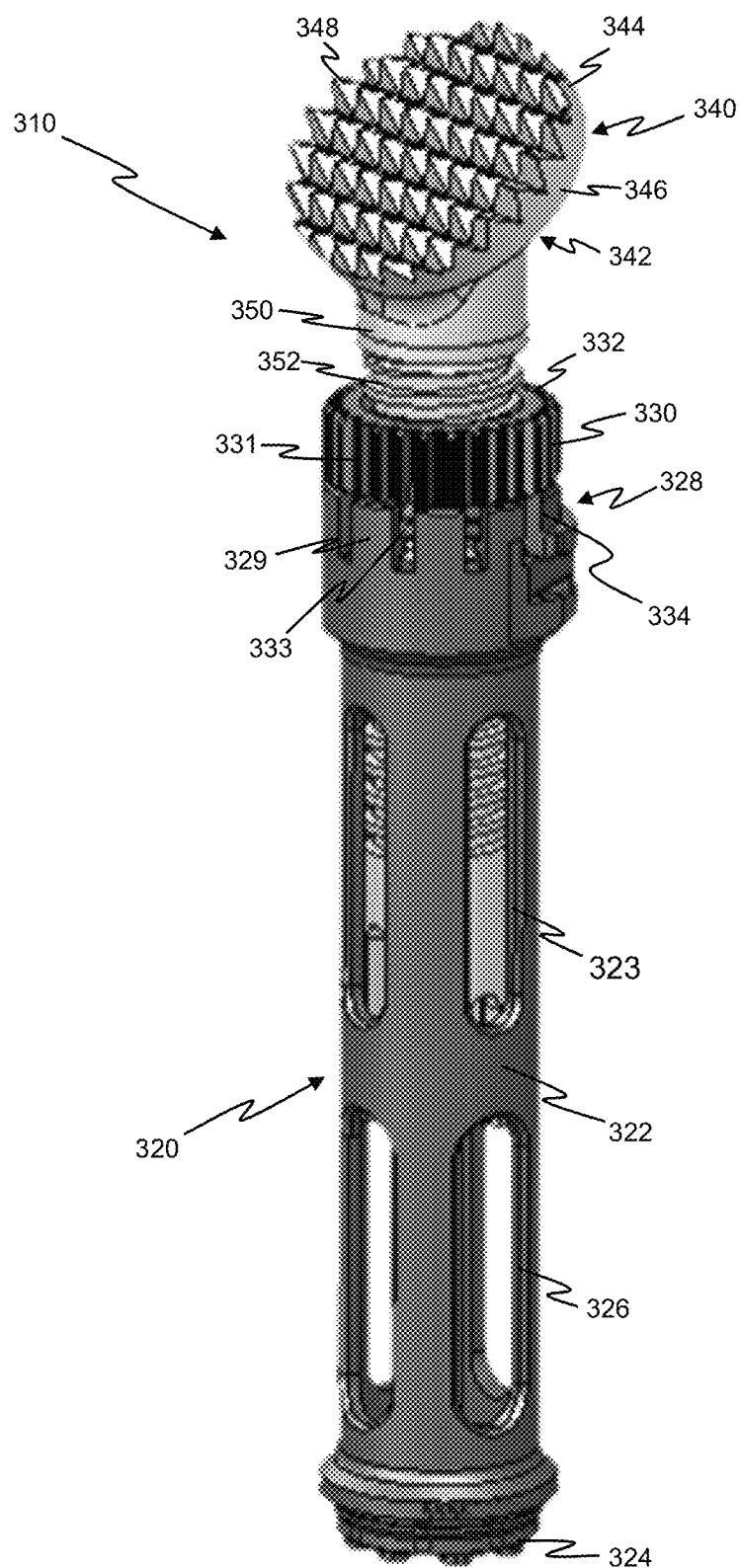
FIG. 10 is a perspective view of an intramedullary nail in accordance with another embodiment of the disclosure.

Referring to FIG. 10, an adjustable intramedullary nail implant 310 in accordance with an embodiment of the disclosure will be described. The implant 310 is adjustable in the proximal-distal direction to facilitate raising and lowering of the humeral head 104. The implant 310 includes a distal portion 320 and a proximal portion 340. A bevel gear assembly 328 at the junction between the distal portion 320 and the proximal portion 340 allows a surgeon to externally adjust the height of the implant through slender instrument. The bevel gear assembly 328 is configured such that upon disconnection of the instrument, the height of the implant 310 is locked. While specific distal and proximal configurations are described herein, it is recognized that the implant 310 may have different options for proximal and distal geometries to allow for a modular design.

In the illustrated embodiment, the distal portion 320 is defined by an elongate hollow shaft 322 extending from a distal end 324 to the bevel gear assembly 328. The proximal end of the distal shaft 322 defines a plurality of fingers 329 with inward projections (not shown) configured to snap fit over a ring 333 of the bevel gear 330 to attach the bevel gear 330 to the shaft 322. As illustrated, the shaft 322 may define one or more slots 323, 326 which facilitate passage of tools, screws and the like.

The bevel gear 330 includes a circumferential body 332 with internal threads (not shown) and external beveled gear teeth 331. The body 332 extends to the ring 333 which snap fits with the shaft fingers 329 such that the bevel gear 330 is rotatably supported relative to the shaft 322. The gear body 332 is coaxial with the axis of the hollow shaft 322. A locking pin 334 is supported on the shaft 322 and is configured to engage the circumferential body 332 and prevent rotation thereof unless an adjustment instrument (not shown) engages the locking pin 334. The adjustment instrument includes a shaft with a rotary gear configured to engage the beveled teeth 331 such that rotation of the instrument causes the gear body 332 to rotate. The adjustment instrument also includes an engagement portion which engages the locking pin 334 and moves it to a disengaged position when the instrument is connected. After the height is adjusted by rotation of the bevel gear 330, the instrument is removed whereby the locking pin 334 automatically moves to the engaged locking position such that the bevel gear is locked in position and the height is fixed.

The proximal portion 340 includes a body 342 defined by a shaft 350 and a head 344. The shaft 350 defines a plurality of external threads 352 configured to threadably engage with the internal threads of the bevel gear 330. The shaft 350 extends through the gear body 332 and into the hollow shaft 322. The shaft 350 is configured such that the shaft 350 does not rotate relative to the hollow shaft 322. As such, with the threadable engagement between the bevel gear 330 and the shaft threads 352, rotation of the bevel gear 330 causes the proximal portion shaft 350 to move proximally or distally. In the illustrated embodiment, the proximal head 344 is defined by a disk 346 supported at an angle relative to the axis of the shaft 350 such that the disk 346 extends medially of a central axis of the shaft 322 and extends into and supports the medial portion of the humeral head 104. A series of sharp protuberances 348 extend from the disk 346 to retain the head 104 onto the nail 310. Additional or alternative means to attach the humeral head 104 to the top of the implant 310 may also be utilized.

Figure 11:
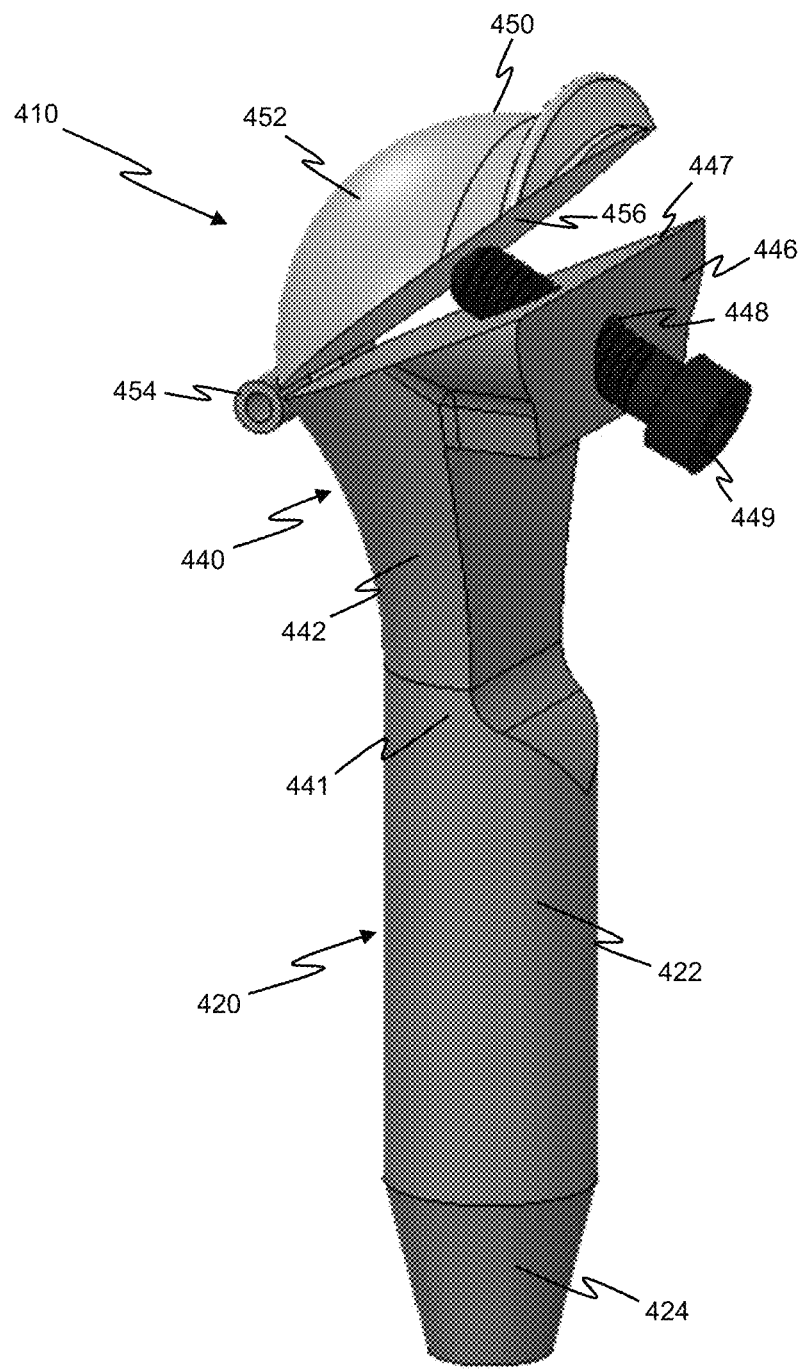
FIG. 11 is a perspective view of an intramedullary nail in accordance with another embodiment of the disclosure.

Referring to FIG. 11, an adjustable intramedullary nail implant 410 in accordance with another embodiment of the disclosure will be described. The implant 410 is configured for varus-valgus adjustment. The implant 410 includes a distal portion 420 and a proximal portion 440. The distal portion 420 is again configured as an elongate shaft or stem which extends from the junction 441 with proximal portion 440 towards the distal portion of the humerus 102. The distal portion 420 may be configured as a cylindrical shaft, however, the shaft may be configured as any geometrical shape (e.g., rectangular, oblong, polygonal, or the like) that suits the intramedullary canal 108. The distal portion 420 forms a body 422 extending to a distal tip 424. In the illustrated embodiment, the distal portion body 422 is a solid structure without holes. With this configuration, the body 422 is preferably manufactured from a material which is penetrable by screws or the like to lock the distal portion in place. Alternatively, the body 242 may have a hollow configuration with screws passing through one wall and into the hollow area. The screws may further extend through the opposite wall. As another alternative, the body 422 may have defined screw holes or slots. The distal portion 420 can also be cemented or press fit in to the canal 108 based on surgeon preference.

The proximal portion 440 of the implant 410 includes a body 442 which extends from the junction 441 to an angled end surface 447. An extending portion 446 of the body 442 defines a screw hole 448 configured to receive an adjustment screw 449 extending laterally. A head component 450 is hingedly connected to the body 442 via the hinge 454. The head component 450 includes a domed proximal surface 452 and an opposite contact surface 456 facing toward the angled end surface 447. The domed proximal surface 452 provides a curved surface which extends medially of a central axis of the shaft 422 such that it extends into and supports the medial portion of the humeral head 104. The adjustment screw 449 contacts the contact surface 456. Advancement of the screw 449 causes the head component 450 to pivot away from the end surface 447. Retraction of the screw 449 causes the head component 450 to pivot toward the end surface 447. Once a desired position of the head component 450 has been achieved, a locking mechanism (not shown) may be engaged to lock the position of the screw and thereby the position of the head component 450. While the body 442 and the head component 450 are illustrated as solid components, it is recognized that one or both may be formed as hollow components or may include screw holes defined therein.

Having described various embodiments of intramedullary nail implants, a method of implanting an intramedullary nail utilizing an external guide in accordance with an embodiment of the disclosure will be described with reference to FIGS. 12-30. The following procedure, although provided in the context of proximal humerus fixation, can be used for periarticular fractures in other anatomical locations. The procedure below shows the use of the device with a solid proximal portion intended for a proximal screw aiming guide, however, the procedure would be identical with a proximal cage except there may not be a need for a proximal aiming guide, only distal.

Figure 12:
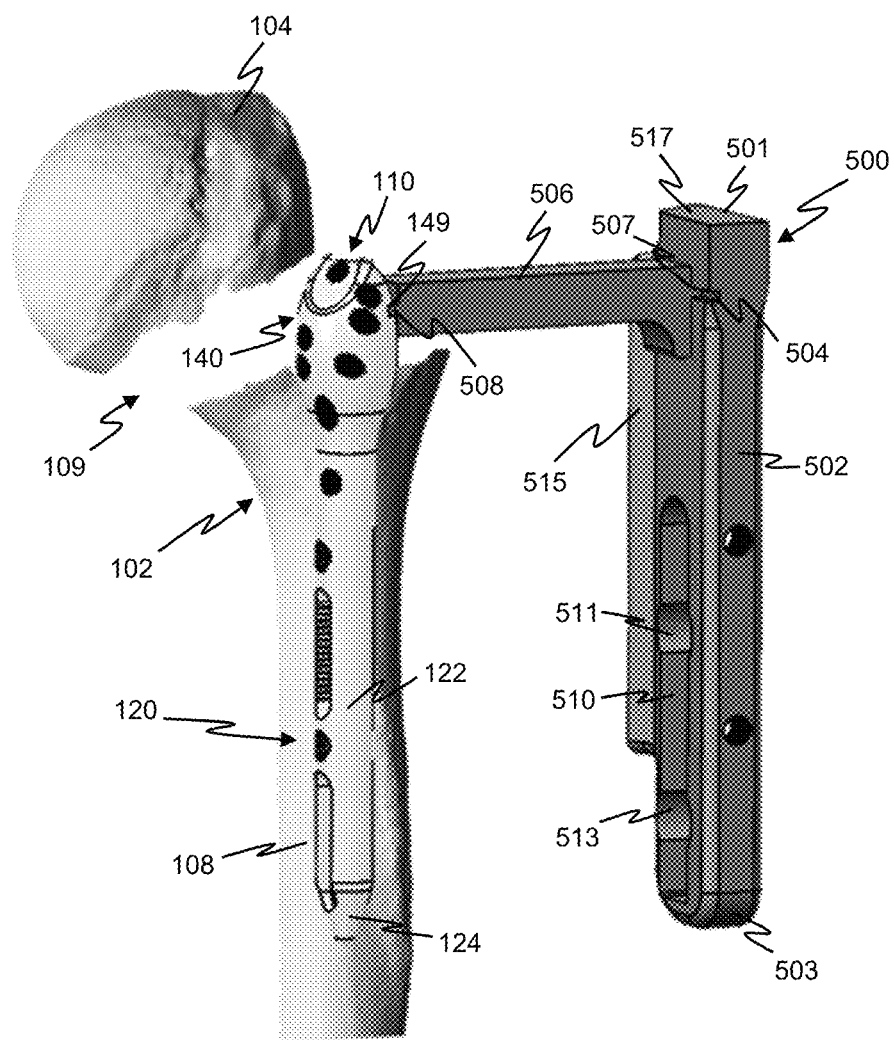
FIGS. 12-30 illustrate a procedure for implanting the intramedullary nail of FIG. 1 utilizing a guide assembly in accordance with an embodiment of the disclosure.

Referring to FIG. 12, an illustrative aiming guide 500 is shown in an initial position relative to the intramedullary nail implant 110. The guide 500 includes longitudinal body 502 extending from a proximal end 501 to a distal end 503. Adjacent the proximal end 501, the body 502 defines an arm attachment slot 504. A connecting arm 506 has a projection 507 configured to slidably engage in the slot 504. An opposite end of the connecting arm 506 has a projection 508 configured to slidably engage in the mounting slot 149 in the proximal portion 140 of the implant 110. With the connecting arm 506 so connected, the implant 110 is maintained in a fixed orientation spaced away from the guide body 502. The distal end 503 of the guide body 502 defines an elongate slot 510 with a pair of through holes 511, 513 extending through the body 502 along the slot 510. It is noted that in the connected position, the slot 510 and holes 511, 513 are aligned with the slots 132, 136 of the implant distal portion 120. The guide body 502 also defines a proximal guide mounting arms 515 and 517, as will be described in more detail hereinafter.

With the implant 110 connected to the connecting arm 506, the implant 110 is ready for implantation. After direct, open access to the fracture (intramedullary canal) has been gained, the implant 110 is slid down the intramedullary canal 108 of the humerus shaft 102 via the fracture site 109. The implant 110 may be moved by direct force thereon, force on the connected guide body 502, or a combination thereof. As the implant 110 is inserted, the slot 510 and holes 511, 513 maintain their alignment with the slots 132, 136 of the implant distal portion 120.

Figure 13:
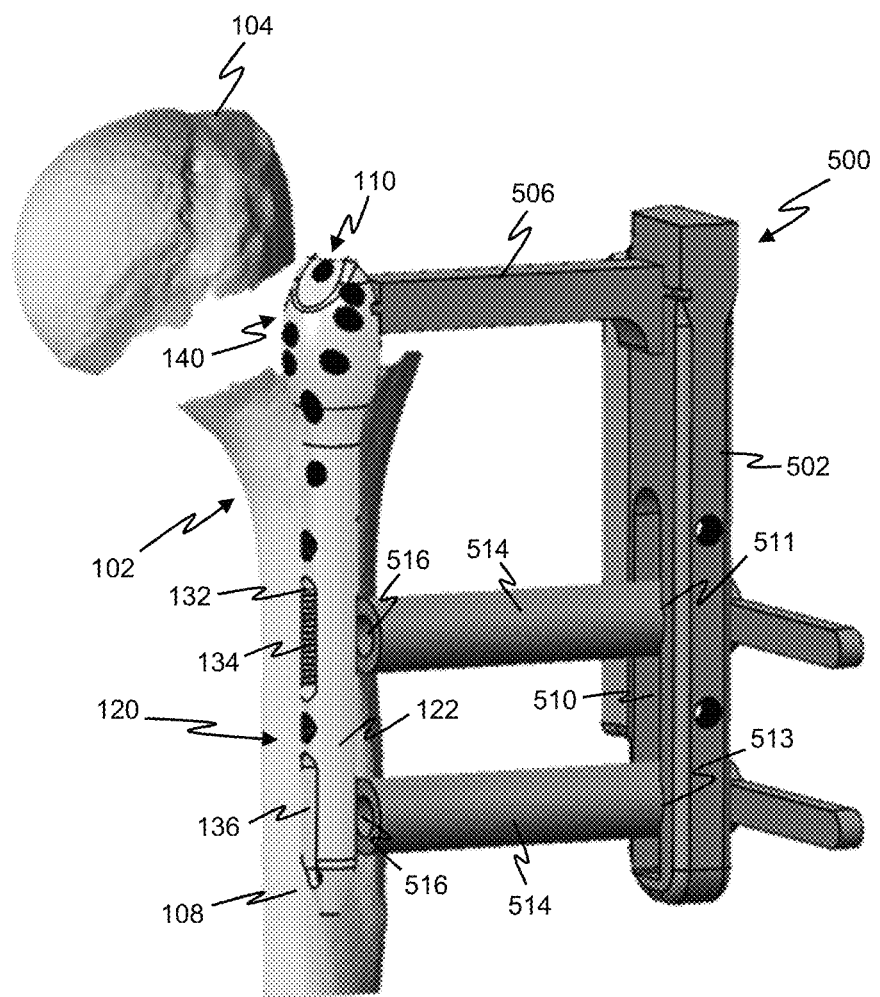

Turning to FIG. 13, once the implant 110 has been properly positioned within the intramedullary canal 108, a distal aiming sleeve 514 is extended through each of the holes 511, 513 of the guide body 502. A through bore 516 of each sleeve 514 is aligned with a respective one of the slots 132, 136 of the proximal portion 120 of the implant 110. A drill bit (not shown) is extended through each sleeve 514 to drill the near cortex of bone.

Figure 14:
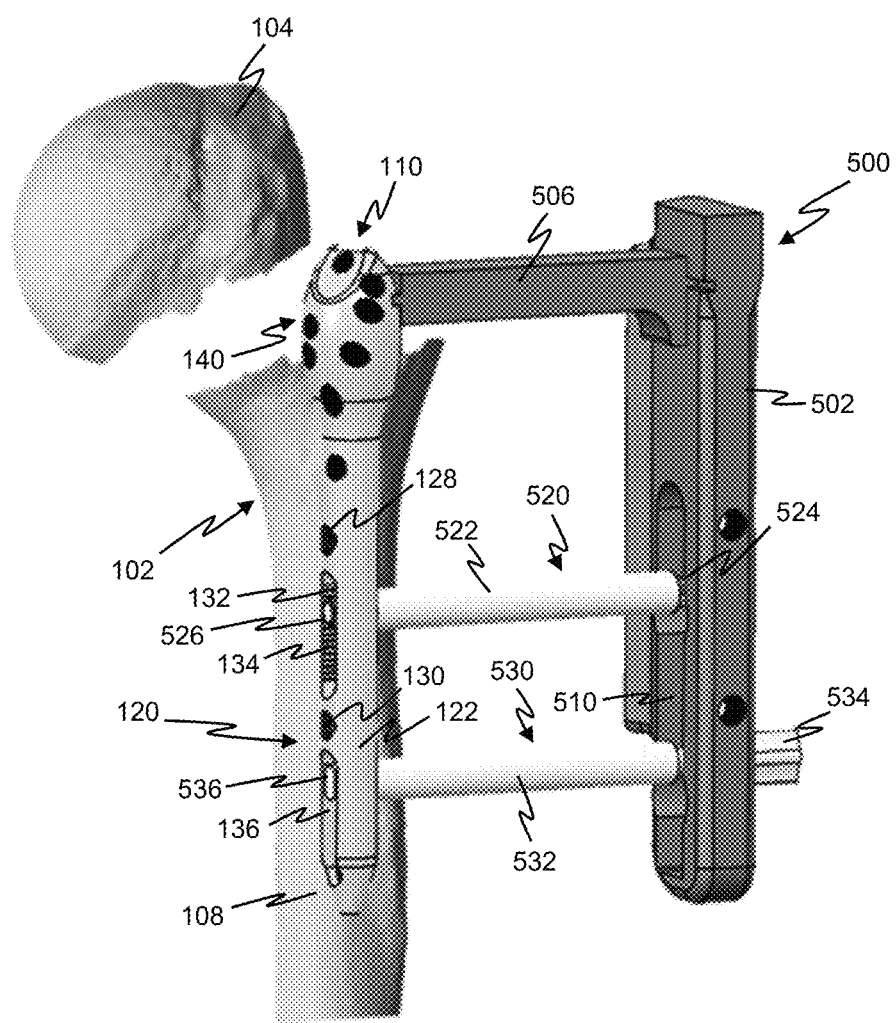
Figures 15, 16:
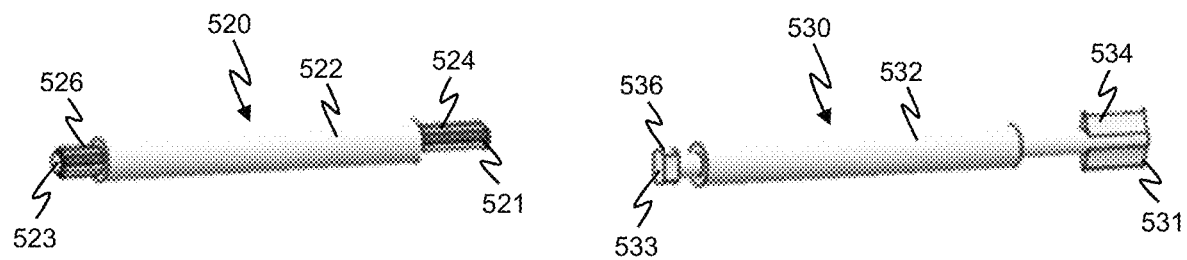
Figure 17:
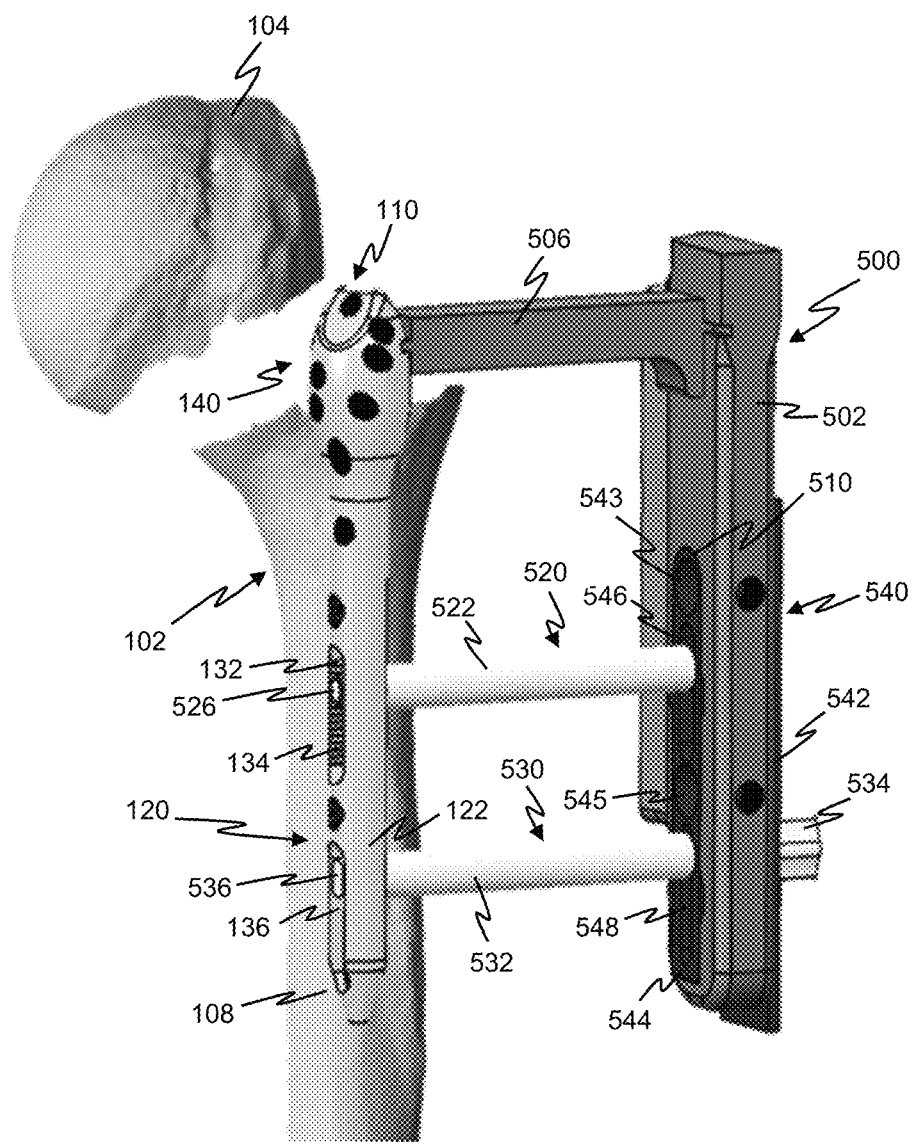

Referring to FIGS. 14-16, a distal pinion gear pin 520 is inserted through the proximal sleeve 514 and the sleeve is removed. Similarly, a distal alignment pin 530 is inserted through the distal sleeve 514 and the sleeve is removed. The distal pinion gear pin 520 includes a shaft 522 extending between ends 521 and 523. Each end 521, 523 has a respective set of pinion teeth 524, 526 defined thereon. The distal alignment pin 530 includes a shaft 532 extending between ends 531 and 533. The first end 531 has an alignment handle 534 defined thereon. The opposite end 533 defines an alignment tab 536 which has a configuration which complements the configuration of the slot 136. When the pins 520, 530 are inserted, the pinion teeth 526 engage the rack teeth 134 in the slot 132 and the alignment tab 536 engages the sides of the slot 136.

Figure 18:
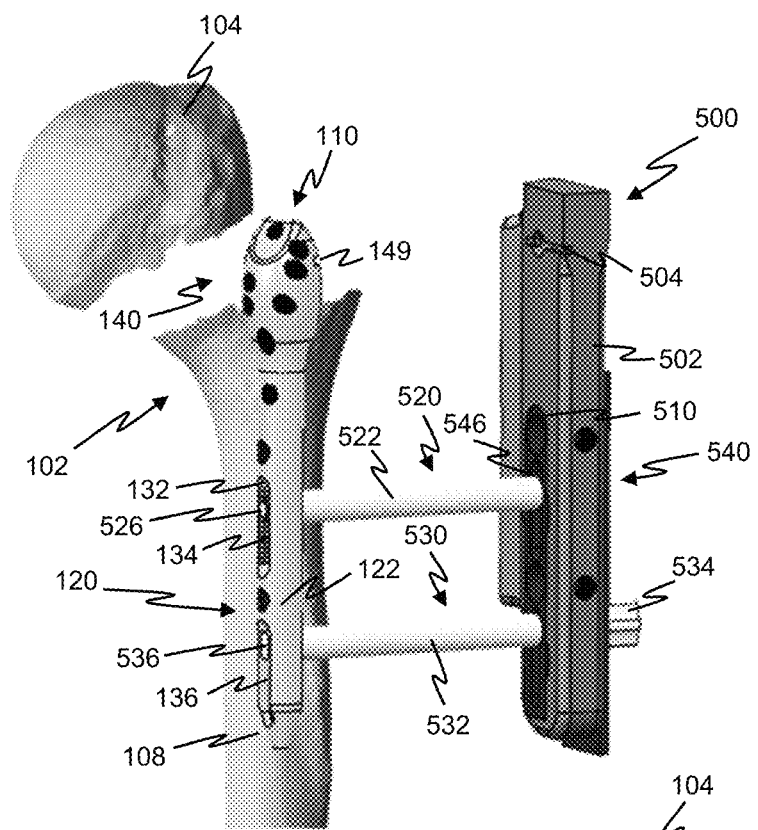
Figure 19:
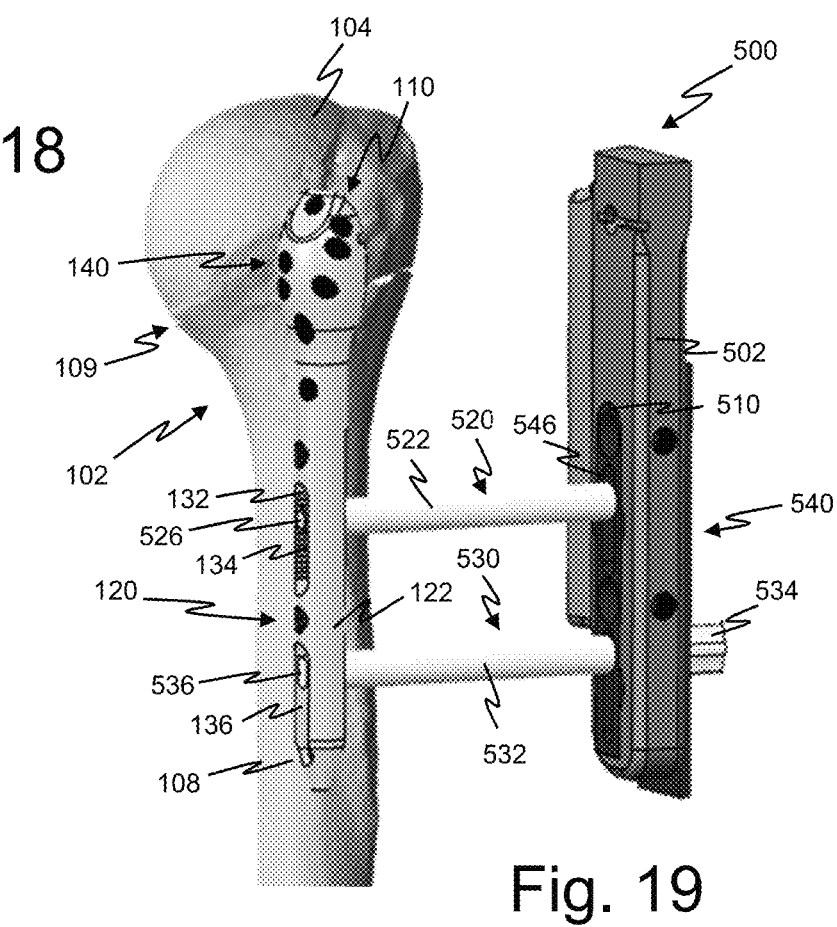
Figure 20:
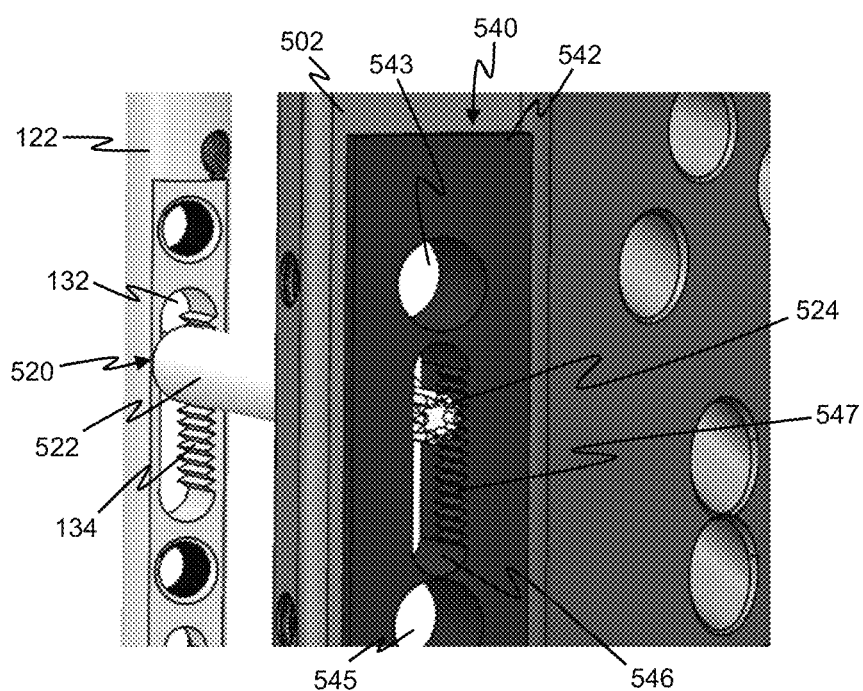

Referring to FIGS. 17-20, a rack insert 540 is engaged with the slot 510 in the guide body 502. The rack insert 540 includes a panel 542 from which an extension 544 extends. The extension 544 has a configuration which generally complements that of the slot 510 such that the extension 544 extends into the slot 510 and is retained in a fixed position. The extension defines a first and second guide bores 543, 545 which are aligned with the holes 128, 130 of the proximal portion 120. The extension also defines a first slot 546 which is aligned with slot 132 of the proximal portion 120 and a second slot 548 which is aligned with slot 136 of the proximal portion 120. As shown in FIG. 20, a series of rack teeth 547, complementing the rack teeth 134, are defined within the slot 546. When the rack insert 540 is engaged, the rack teeth 547 engage the pinion teeth 524 of the distal pinion gear pin 520. With the pinion teeth 524, 526 engaged with the rack teeth 547, 134 respectively, the distal pinion gear pin 520 defines the relative position between the guide body 502 and the implant 110. At this time, the connecting arm 506 is slidably removed as shown in FIG. 18. After the connecting arm 506, has been removed, the fracture is reduced as shown in FIG. 19.

Figure 21:
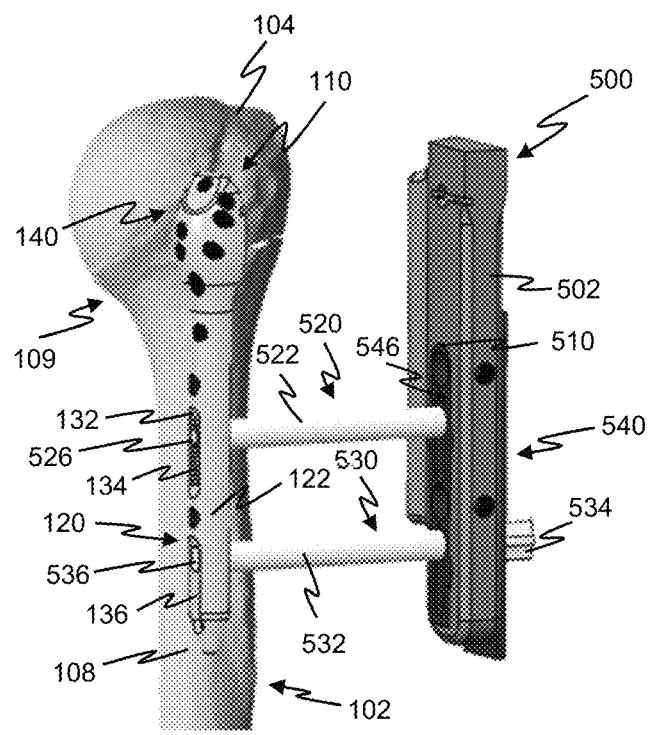
Figure 22:
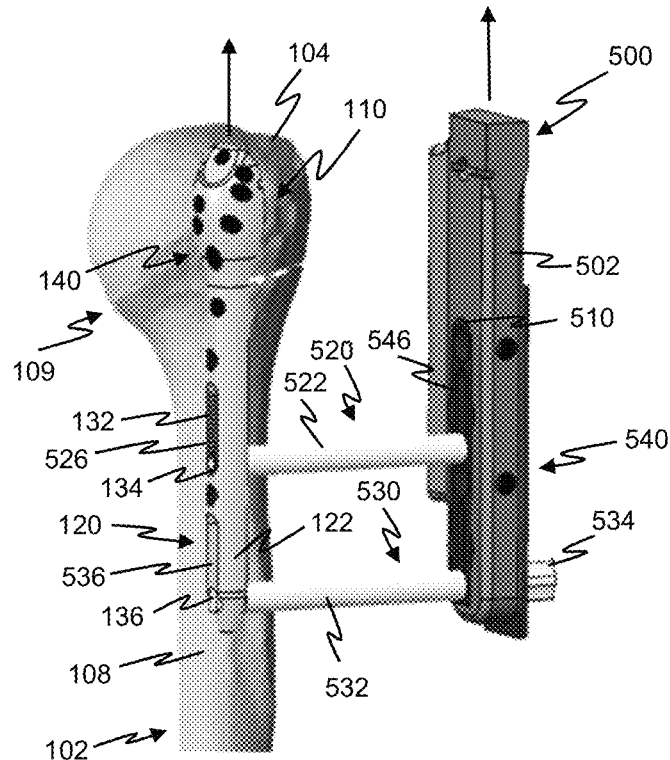
Figure 23:
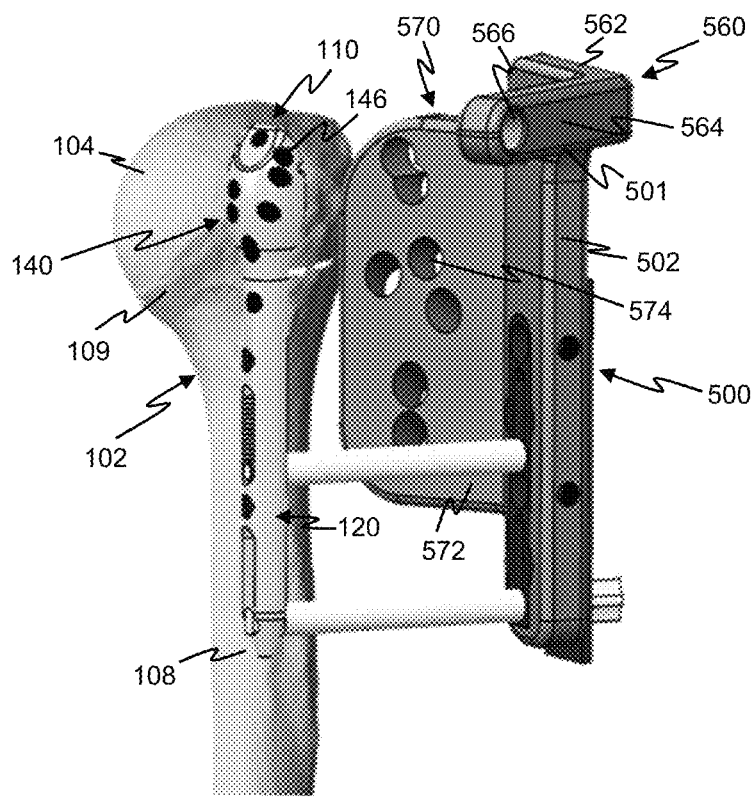
Figure 24:
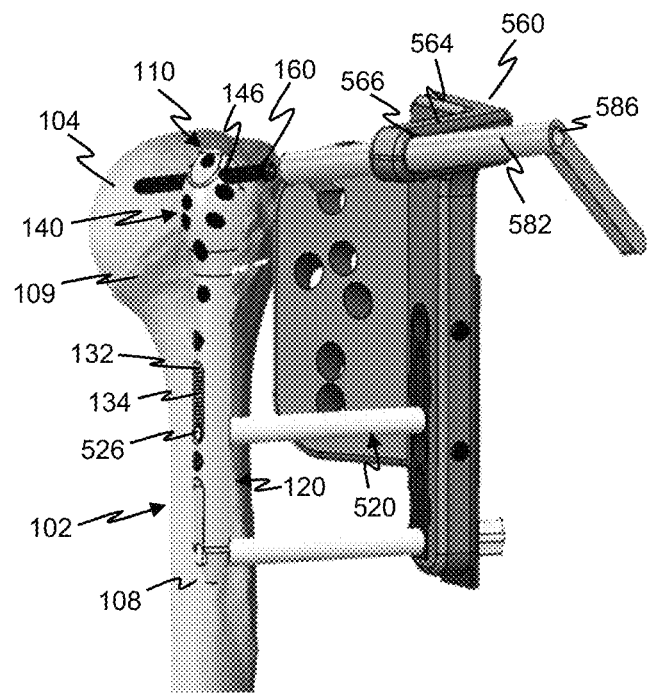

Referring to FIGS. 20-22, proximal/distal adjustment of the implant 110 will be described. Since the distal pinion gear pin 520 extends through a hole in the bone 102, the pin 520 may not move proximally/distally, but can only rotate. As such, with the pinion teeth 524, 526 are engaged with the rack teeth 547, 134 respectively, as shown in FIG. 20, movement of the guide body 502 will cause the distal pinion gear pin 520 to rotate which will in turn cause the implant 110 to move with the guide body 502. Comparing FIG. 21, showing the initial position, with FIG. 22, as the guide body 502 is moved proximally, the implant 110 moves a corresponding amount in the proximal direction. The implant 110 and the guide body 502 translate may together so that when the proximal guides are attached and the surgeon is ready to drill holes, the guide body 502 and the implant 110 are able to maintain orientation to accurately target screw holes 146. This may also be helpful for distal aiming.

Figure 25:
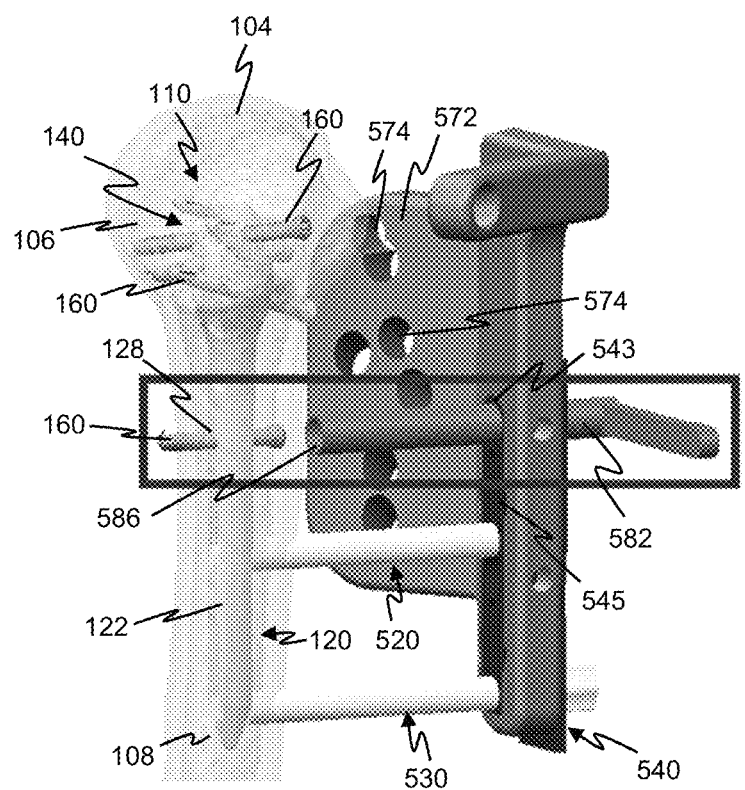
Figure 26:
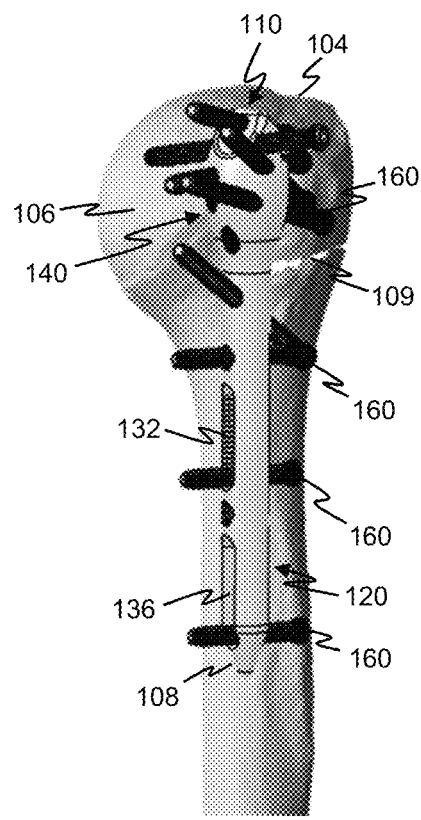

With the implant 110 adjusted to the proper position, the proximal and distal screws are inserted as shown in FIGS. 23-26. First, the proximal aiming guides 560, 570 are attached to the proximal guide mounting arms 517 and 515, respectively. The proximal aiming guide 560 includes a body 562 with an extending arm 564. The extending arm 564 defines a guide hole 566 which is aligned with one of the screw holes 146 of the proximal portion 140 of the implant 110. A guide sleeve 582 is positioned through the guide hole 566 such that a through passage 586 thereof is aligned with the screw hole 146. A screw 160 is then extended through the through passage 586 and drilled into the bone 102 and the screw hole 146. Similarly, the proximal aiming guide 570 includes a planar body 562 which defines a plurality of guide holes 574, each of which is aligned with one of the screw holes 146 of the proximal portion 140 of the implant 110. Again, a guide sleeve 582 may be positioned through each guide hole 574 to insert a screw into the respective screw hole 146. Additionally, the guide sleeve 582 may be positioned through the holes 543, 545 through the rack insert 540 to insert screws 160 in the holes 128, 130, as shown in FIG. 25. Additionally, once the position of the implant 110 has been fixed relative to the bone 102, the pins 520, 530 may be removed and screws 160 inserted in their place, as shown in FIG. 26.

There may exist a need to make the connection between the implant 110 and the guide assembly 500 more rigid for screw targeting. Once the proximal distal adjustment has been made, it is necessary that the relative position between the implant and guide is maintained. If this positioning is not maintained, screws will collide with or miss the device and not lock into the device.

Figure 27:
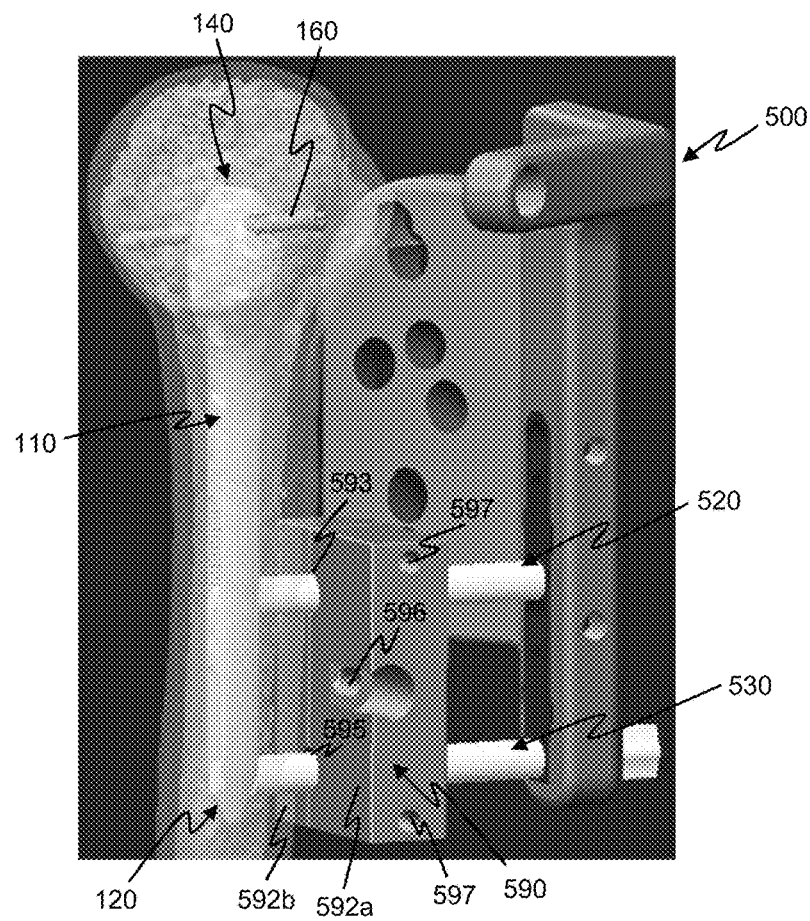
Figure 28:
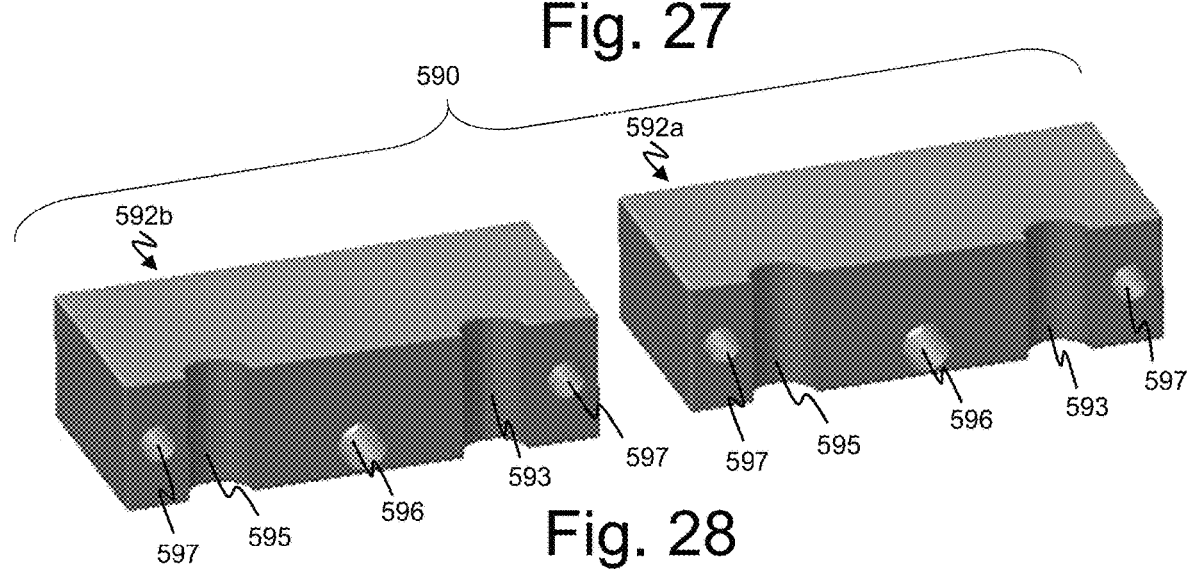

Referring to FIGS. 27 and 28, one way to achieve more rigidity is to have a support block 590 positioned closer to the bone that aligns the distal pins 520, 530 while letting them spin freely. In the illustrated embodiment, the support block 590 comprises two halves 592a, 592b, each defining half of the pin holes 593, 595. Once the block halves 592a, 592b are positioned in abutment with the pins 520, 530 extending through the pin holes 593, 595, screws or the like are secured in holes 596, 597 to secure the halves 592a, 592b together. Alternatively, the support block may be made as one piece with a hinge to facilitate positioning about the pins 520, 530.

Figure 29:
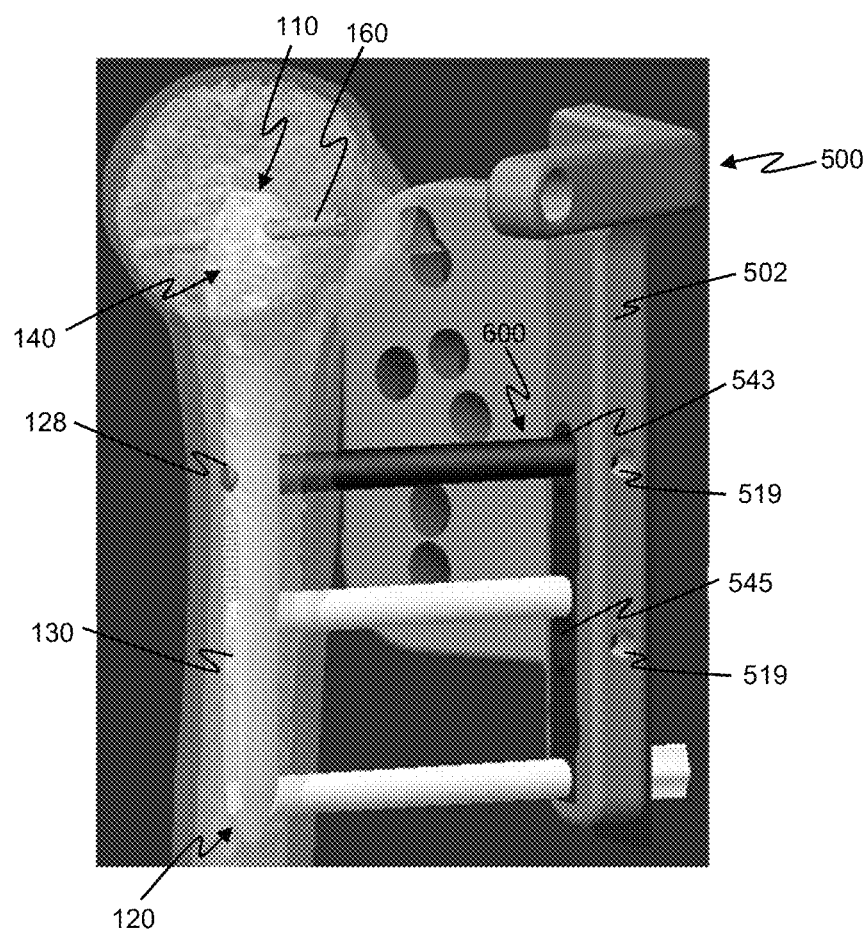
Figure 30:
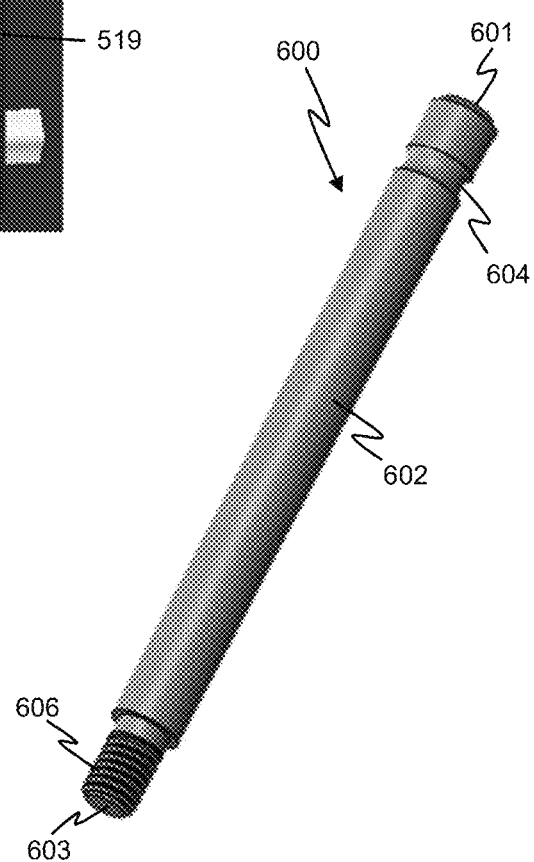

Referring to FIGS. 29 and 30, another method to achieve extra stability before aiming proximal screws is to add one or more extra distal posts 600 after proximal/distal adjustment has been achieved. The posts 600 includes a shaft 602 extending between ends 601 and 603. The end 603 that engages the implant 110 includes threads 606 for threaded engagement in one of the holes 128, 130. The threads 606 may have a tapered thread design so that if the implant and guide assembly 500 are not perfectly aligned, the post 600 will be "self-aligning." The opposite end 501 of the post 600 includes a radial groove 604 which aligns with set screw holes 519 on the side of the guide body 502. A set screw (not shown) engages the groove 604 and locks the post 600 relative to the guide body 502.

Figure 31:
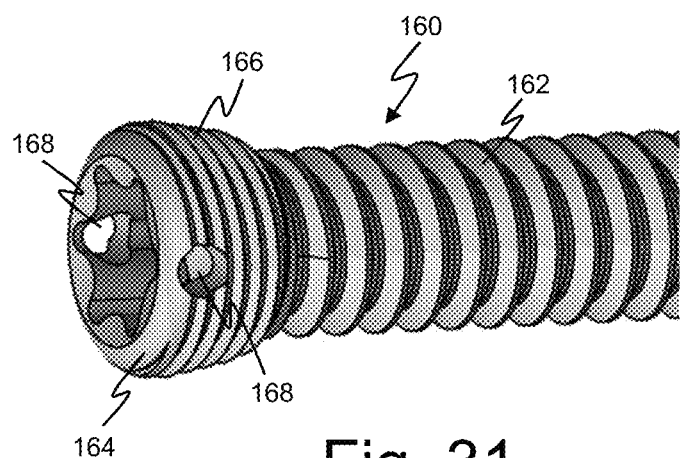
FIGS. 31-37 illustrate screw assemblies in accordance with embodiments of the disclosure.

The screws 160 utilized herein may have screw heads 164 with some means of attaching suture to the screw 160. This may be useful for proximal humerus fracture fixation because surgeons can utilize sutures to control the rotator cuff which is connected to the tuberosity bone fragments of the proximal humerus. Referring to FIG. 31, the screw 160 includes a threaded shaft 162 and a screw head 164 with threads 166. Suture fixation holes 168 may be drilled directly into the head 164 of the screw 160, for example.

Figure 32:
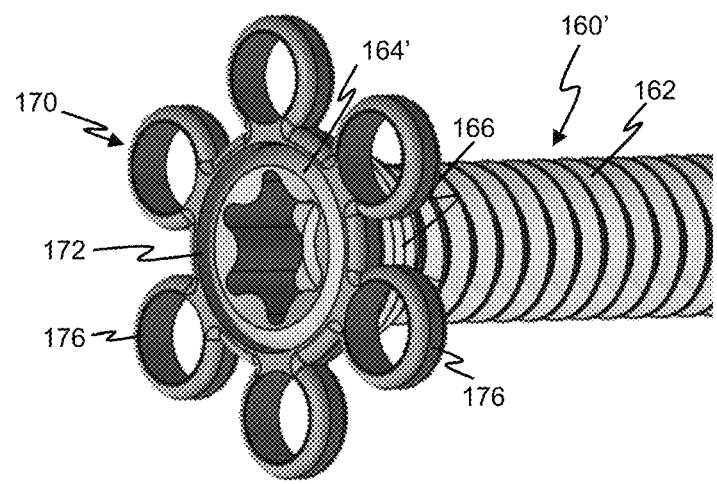
Figure 33:
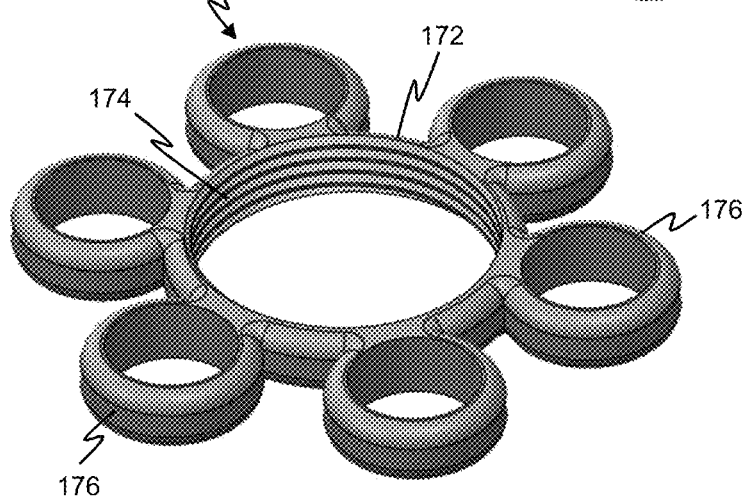

Referring to FIGS. 32 and 33, an alternative screw 160' with suture loops 176 will be described. The screw 160 includes again includes a threaded shaft 162 and a head 164', however the head 164' does not include suture holes. Instead, a suture ring 170 is threadably engaged with the threads 166 of the screw head 164'. The suture ring 170 has a ring body 172 which defines internal threads 174 configured to engage with the screw head threads 166. One or more suture loops 176 extend from the ring body 172. The suture ring 170 may be attached to the screw head 164' after the screw 160' has been inserted in the bone.

Figure 34:
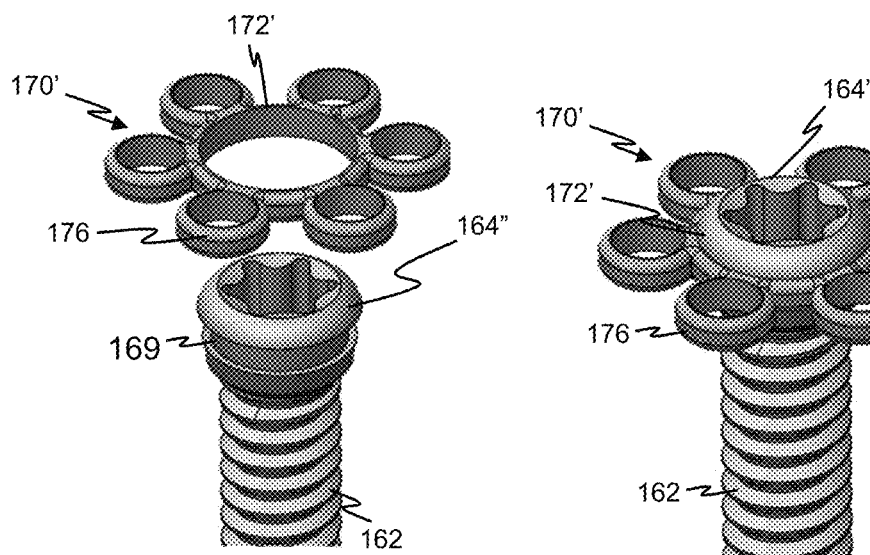
Figure 35:
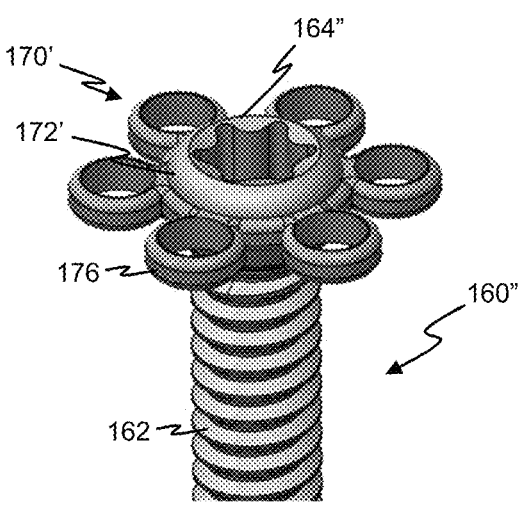

FIGS. 34 and 35 illustrate an alternative suture ring 170' embodiment. In the present embodiment, the ring body 172' is free of internal threads. Instead, the screw head 164" of screw 160" defines a circumferential groove 169. The ring body 172' is snap fit into the groove 169. Again, the suture ring 170' may be attached to the screw head 164" after the screw 160" has been inserted in the bone.

Figure 36:
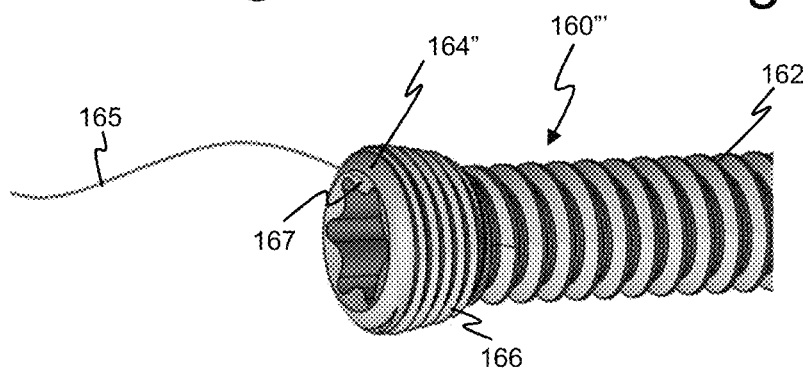

With reference to FIG. 36, a screw 160'" with a pre-attached suture 165 in accordance with an embodiment of the disclosure will be described. As illustrated, the screw 160'" includes a threaded shaft 162 and a screw head 164'". The suture 165 is welded, glued or otherwise attached directly to the screw head 164 as illustrated at 167.

Figure 37:
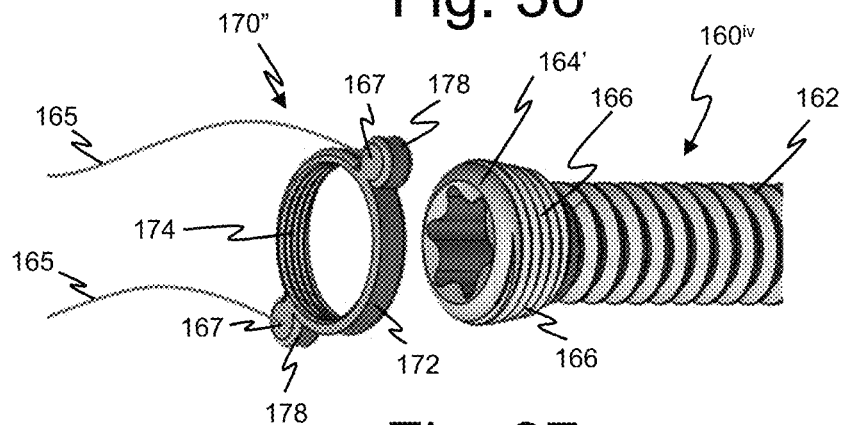

Another screw 160iv configured for suture attachment is illustrated in FIG. 37. As shown therein, the screw 160iv includes a threaded shaft 162 and a screw head 164' with external threads 166. A suture ring 170" is configured for attachment to the screw head threads 166. The suture ring 170" includes a ring body 172 with internal threads 174 configured to threadably engage the screw head threads 166. At least one tab 178 extends from the ring body 172 and the suture 165 is welded, glued or otherwise attached directly to the tab 178 as illustrated at 167. The ring body 172 may be attached via thread or a snap in mechanism as described above. It may also thread into an internal thread inside the drive feature of the screw head 164'.

Referring to FIGS. 38-42, another method of implanting an intramedullary nail utilizing an external guide in accordance with an embodiment of the disclosure will be described. The following procedure, although provided in the context of proximal humerus fixation, can be used for periarticular fractures in other anatomical locations.

Figure 38:
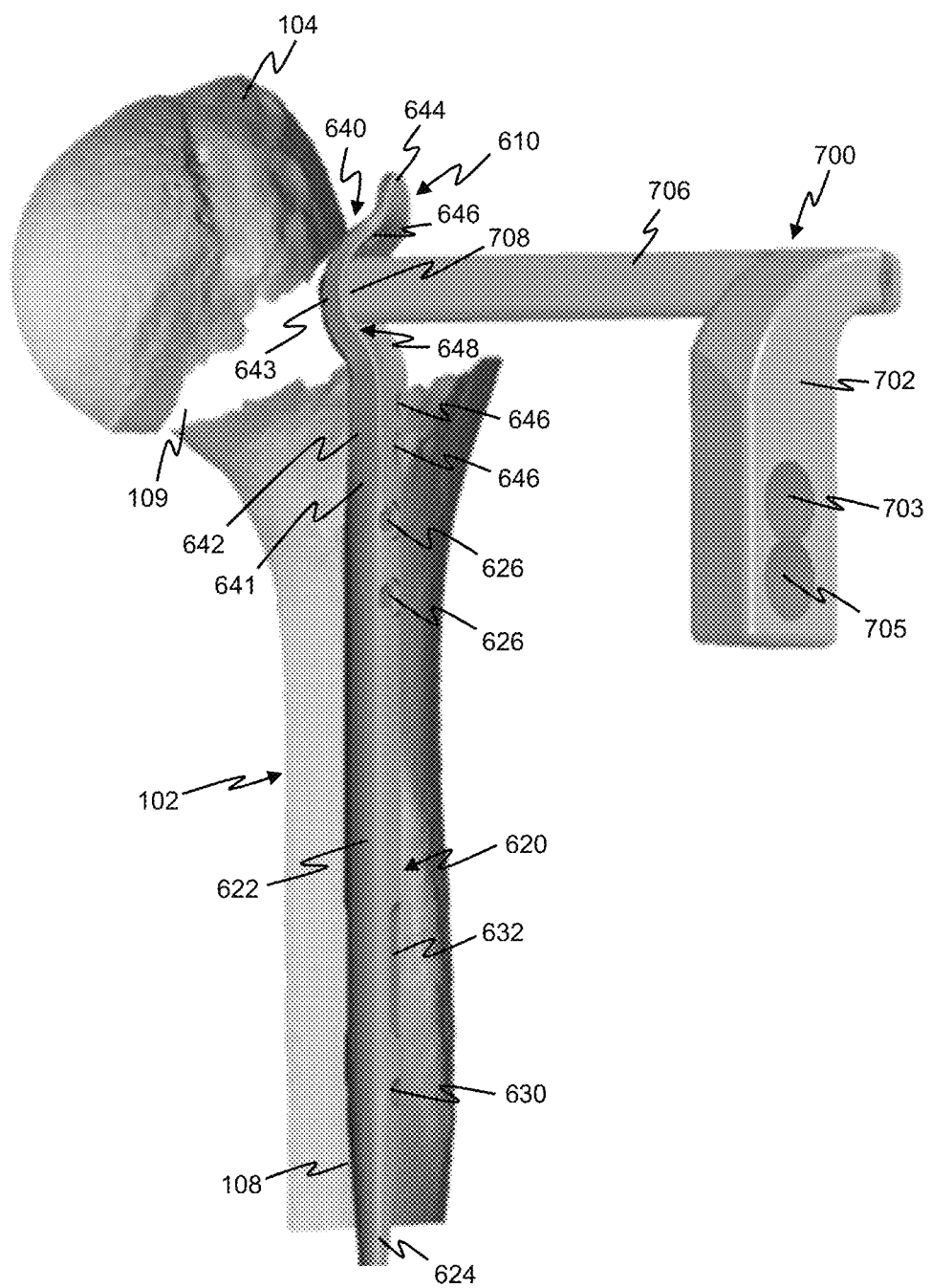
FIGS. 38-42 illustrate a procedure for implanting an intramedullary nail utilizing a guide assembly in accordance with an embodiment of the disclosure.

With reference to FIG. 38, the intramedullary nail implant 610 utilized with the described method includes a distal portion 620 and a proximal portion 640. The distal portion 620 is again configured as an elongate shaft or stem which extends from the junction 641 with proximal portion 640 towards the distal portion of the humerus 102. The distal portion 620 may be configured as a cylindrical shaft, however, the shaft may be configured as any geometrical shape (e.g., rectangular, oblong, polygonal, or the like) that suits the intramedullary canal 108. The distal portion 620 forms a body 622 extending to a distal tip 624. In the illustrated embodiment, the distal portion body 622 includes screw holes 626 and 630 and a slot 632.

The proximal portion 640 of the implant 610 includes a body 642 extending to a proximal end 644. A curved portion 643 of the body 642 is defined adjacent the proximal end 644. The curved portion 643 provides a curved surface which extends medially of a central axis of the shaft 622 such that it extends into and supports the medial portion of the humeral head 104. The curved portion 643 also defines an internal cup 648 configured to receive a portion of the alignment assembly 700, as will be described hereinafter. A plurality of screw holes 646 are defined through the proximal portion body 642.

Figure 41:
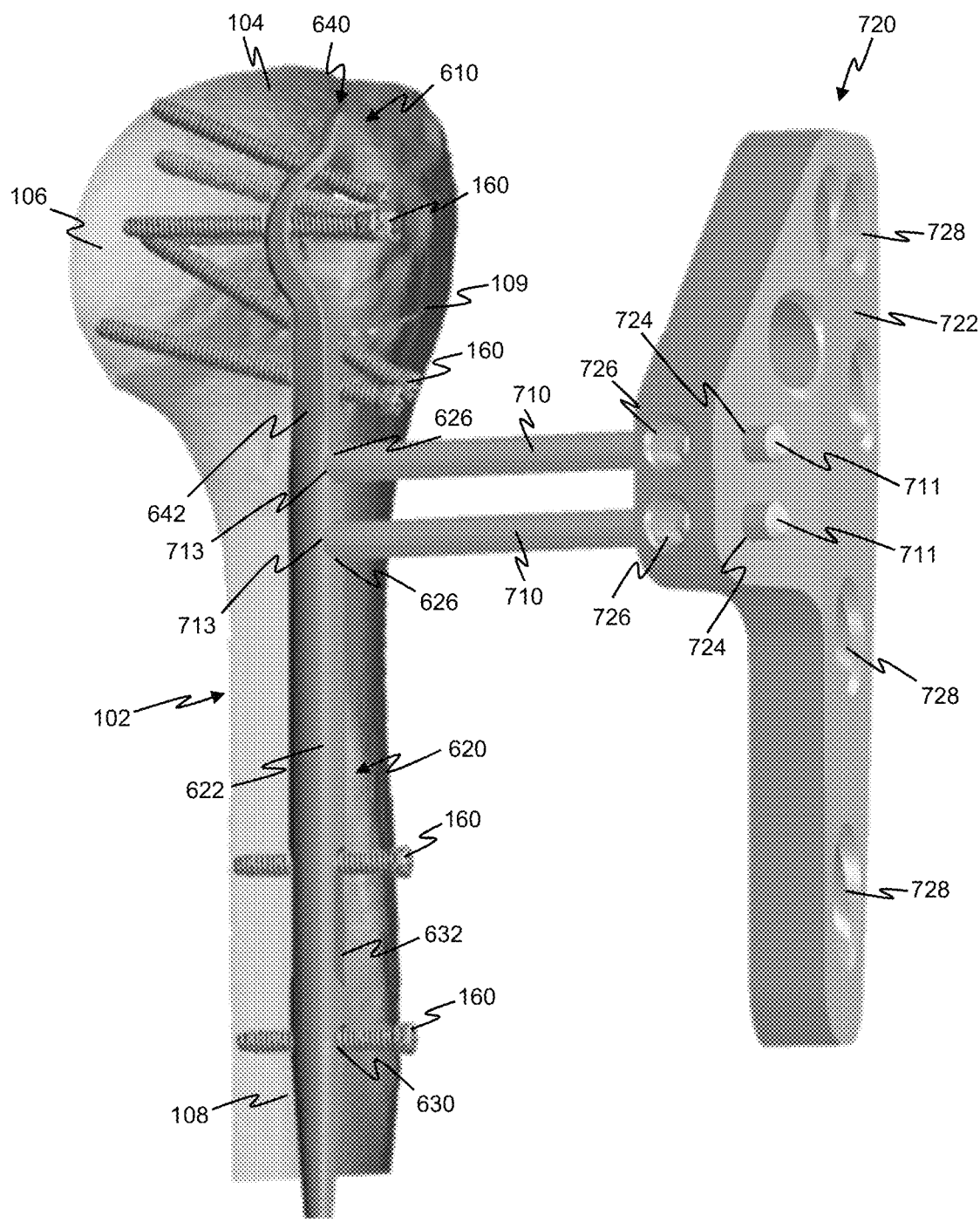

For implantation utilizing this method, two separate guides are utilized, namely an alignment guide 700 shown in FIG. 38 and an aiming guide 720 shown in FIG. 41. The alignment guide 700 includes a body 702 defining a pair of guide holes 703, 705. An alignment arm 706 extends from the body 702 to a free end 708. The alignment guide 700 is configured such that when the free end 708 of the alignment arm 706 is positioned in the cup 648, the guide holes 703, 705 align with the holes 626 of the proximal portion of the implant 610.

To begin the procedure, after direct, open access to the fracture (intramedullary canal) has been gained, the implant 610 is slid down the intramedullary canal 108 of the humerus shaft 102 via the fracture site 109. The implant 610 is generally inserted by direct force thereon. Once the implant 610 is inserted to a desired position, the free end 708 of the alignment arm 706 is positioned in the cup 648 such that the guide holes 703, 705 align with the holes 626 of the proximal portion of the implant 610, as shown in FIG. 38.

Figure 39:
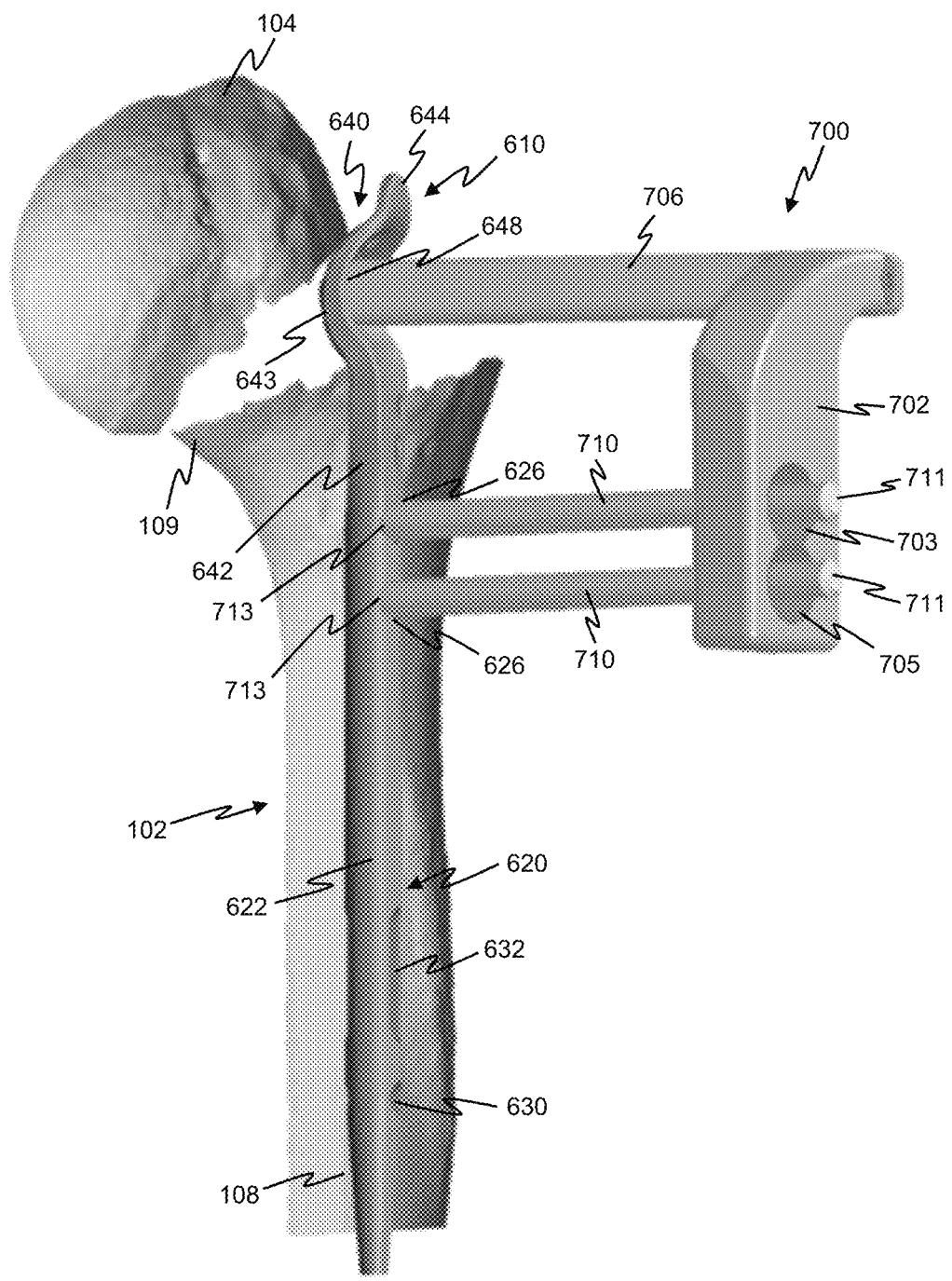

With the alignment guide 700 in place, a distal post 710 is passed through each guide hole 703, 705 and into threaded engagement with a respective distal portion hole 626, as shown in FIG. 39. Each distal post 710 extends from a free end 711 to a threaded end 713. A guide sleeve (not shown) may be utilized for positioning of each of the distal posts 710.

Figure 40:
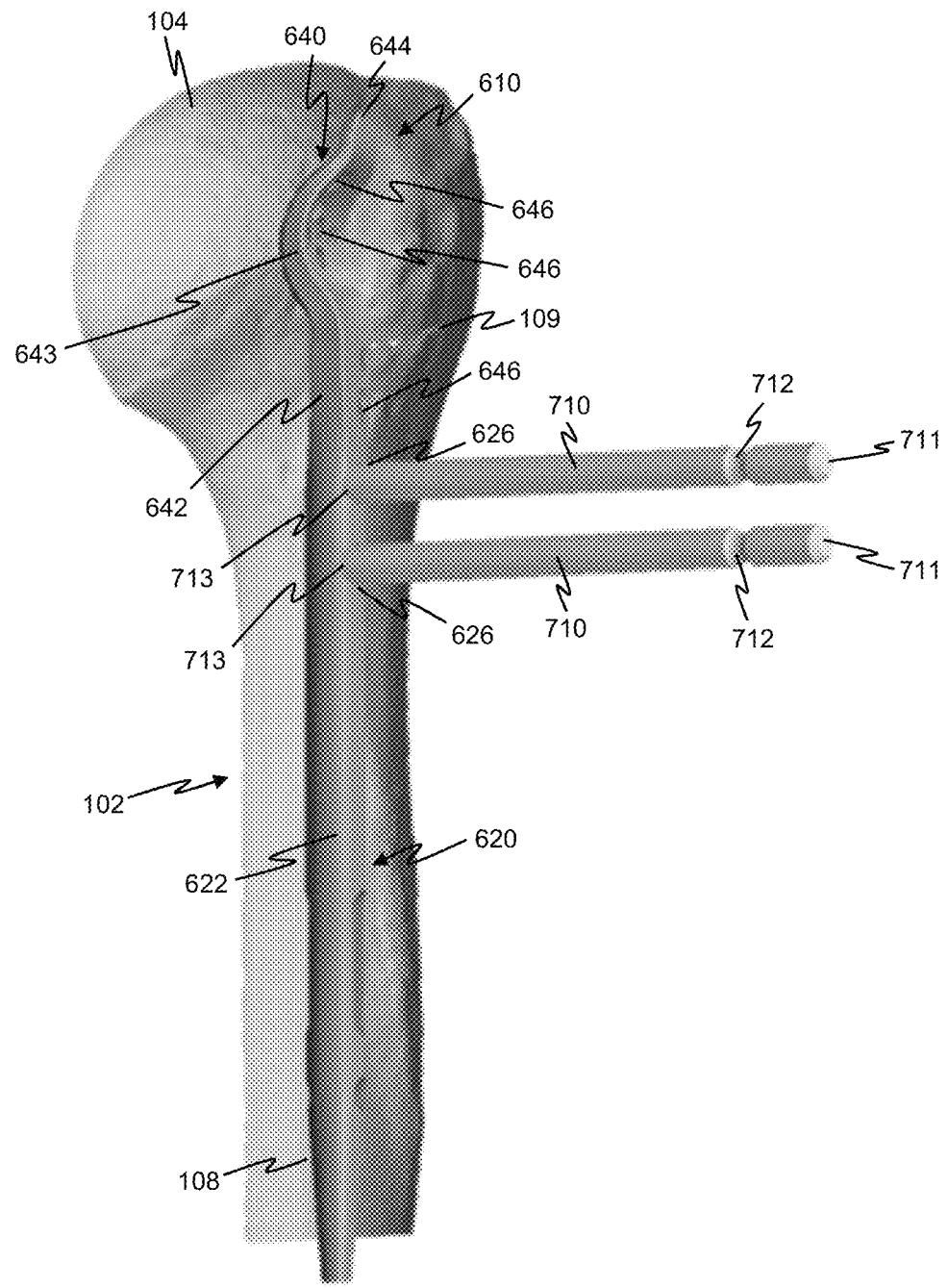

Turning to FIG. 40, once the distal posts 710 are positioned, the alignment guide 700 is removed from the posts 710 and engagement with the cup 648. With the alignment guide 700 removed, the fracture may then be reduced.

Figure 42:
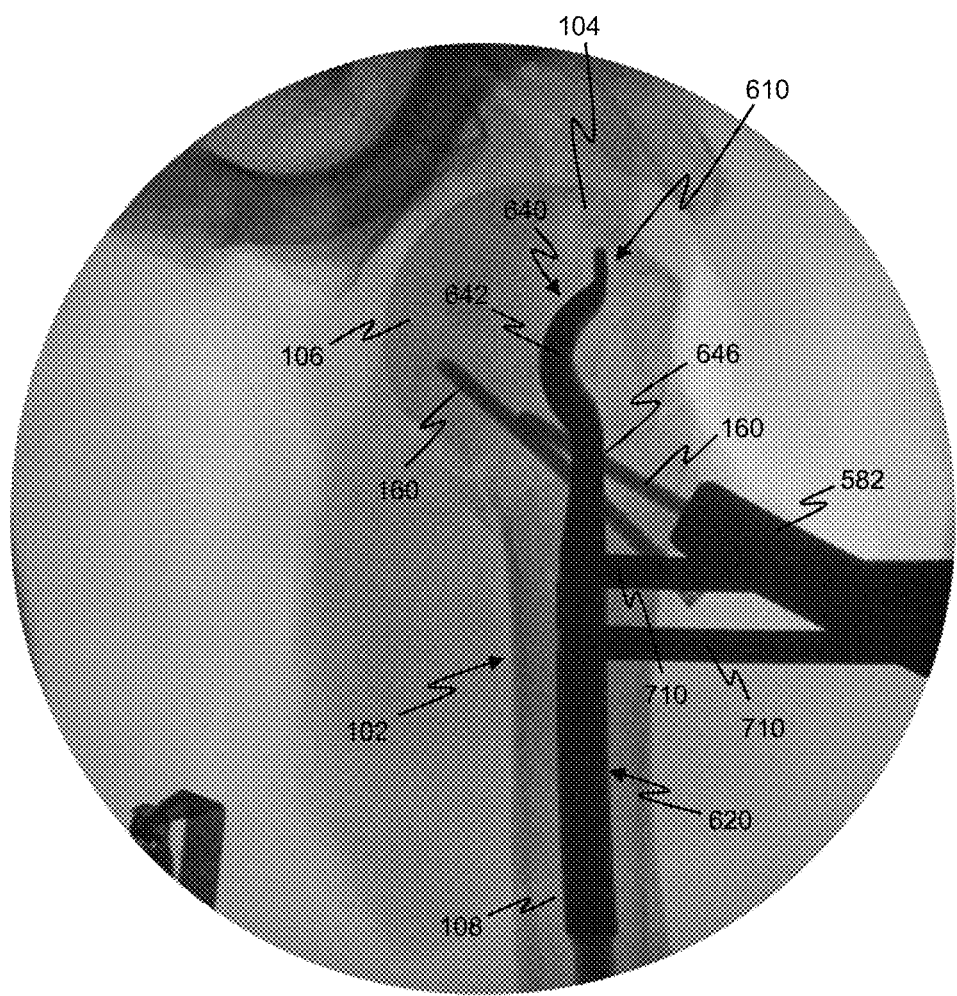
Figure 43:
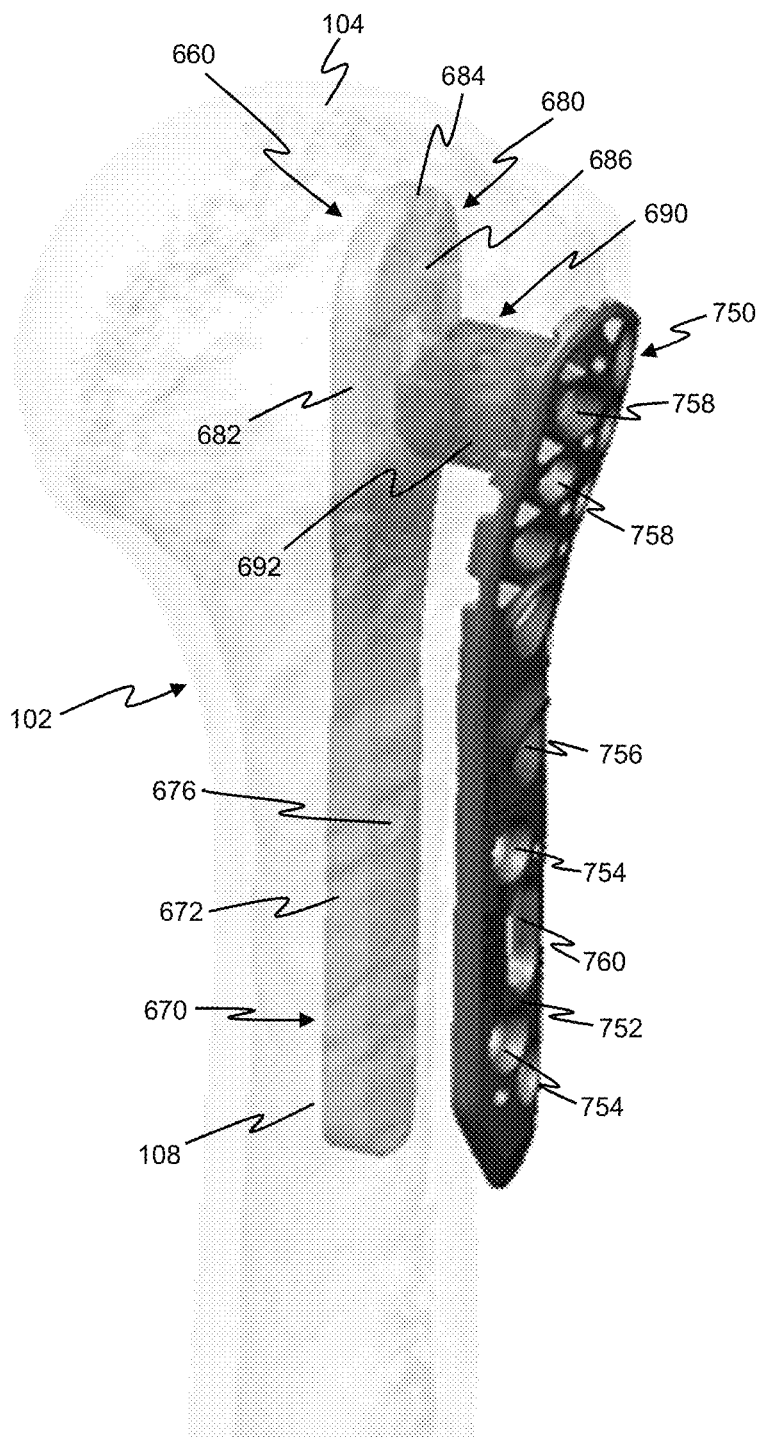
FIG. 43 illustrates a procedure for implanting an intramedullary nail utilizing a bone plate and spacer in accordance with an embodiment of the disclosure.

Referring to FIGS. 41 and 42, the aiming guide 720 is positioned on the posts 710. The aiming guide 720 includes a body 722 defining a pair holes 724 which align with and receive the free ends 711 of the distal posts 710. In this way, the posts 710 align the aiming guide 720 with the implant 610. Set screws or the like may be positioned in holes 726 in the side of the body 722 and engage grooves 712 (see FIG. 40) near the free end 711 of each post 710 to lock the aiming guide 720 in place. A plurality of guide holes 728 extend through the body 722, with each guide hole 728 aligned with a respective screw hole 630, 646 of the implant 610. Screws 160 are then inserted through guide sleeve 582 positioned in the guide holes 728 as shown in FIG. 42. Once the screws 160 are inserted, the posts 710 may be removed and screws 160 may be optionally inserted in the holes 626. While the alignment guide 700 and aiming guide 720 are illustrated as separate components, it is understood, the functionality can be provided in a single guide with a removable arm, similar to the guide assembly above.

Figures 44, 45:
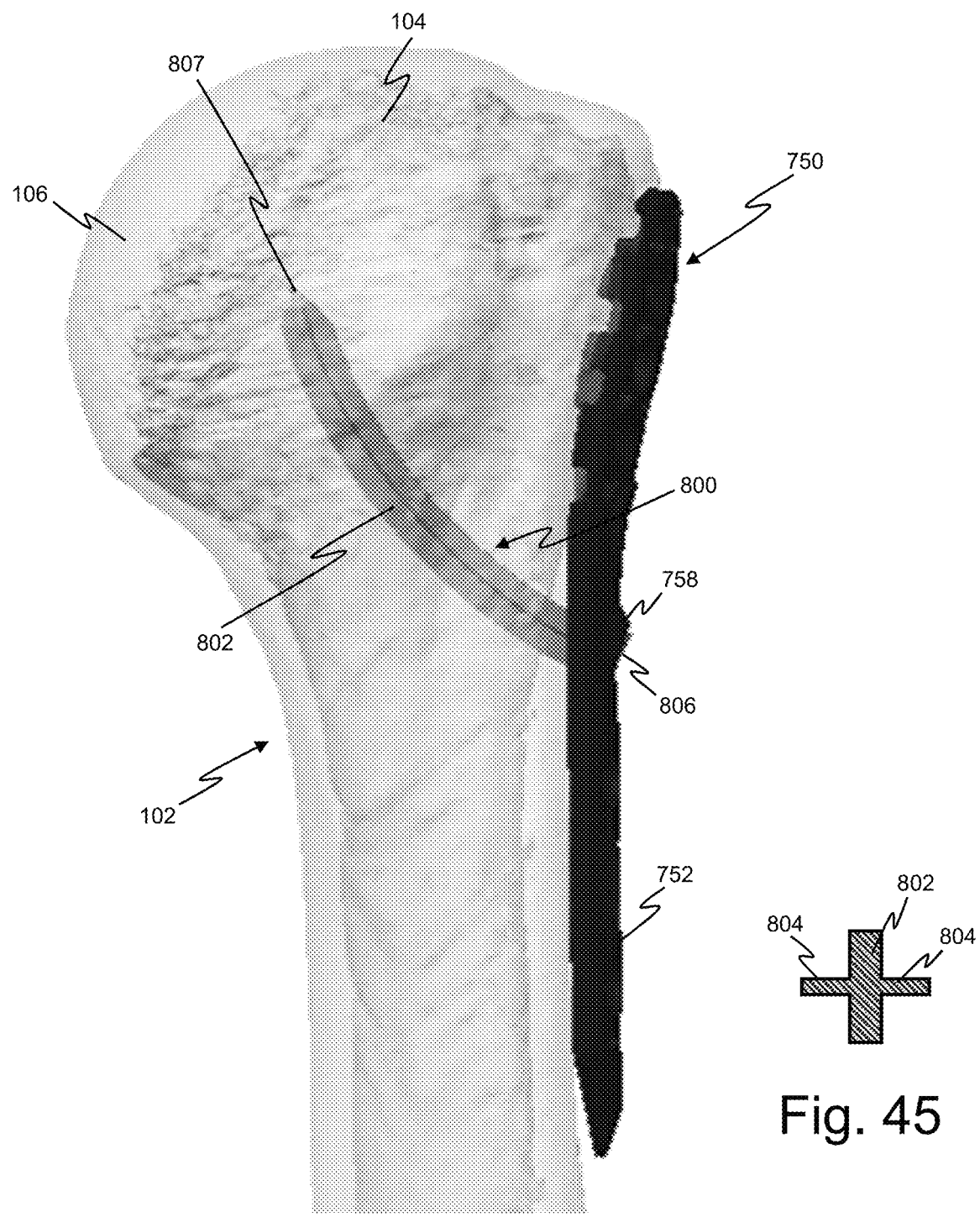
FIGS. 44-47 illustrate a calcar blade in accordance with an embodiment of the disclosure.

Referring to FIG. 44, another method of implanting an intramedullary nail utilizing an external structure in accordance with an embodiment of the disclosure will be described. The following procedure, although provided in the context of proximal humerus fixation, can be used for periarticular fractures in other anatomical locations.

In the present embodiment, a proximal humerus plate 750 is utilized in conjunction with the intramedullary nail implant 660 and the plate 750 acts as the aiming guide. The humerus plate 750 includes a plate body 752 which may have various configurations. Illustrative plate configurations are shown in the '044 application and the humerus plate 750 may have one of such illustrated configurations or a different configuration. The plate body 752 defines a plurality of holes 754, 756, 758 and a slot 760.

The illustrated intramedullary nail implant 660 includes a distal portion 670 and a proximal portion 680. The distal portion 670 is again configured as an elongate shaft or stem 672 which extends from the junction with proximal portion 680 towards the distal portion of the humerus 102. The distal portion 670 may be configured as a cylindrical shaft, however, the shaft may be configured as any geometrical shape (e.g., rectangular, oblong, polygonal, or the like) that suits the intramedullary canal 108. In the illustrated embodiment, the distal portion 670 includes screw holes 676. The proximal portion 680 of the implant 660 includes a body 682 extending to a proximal end 684. A plurality of screw holes 686 are defined through the proximal portion body 682. The screw holes 676, 686 in the implant 660 are positioned to align with at corresponding holes 754, 756, 758 and/or slot 760 in the humerus plate 750.

Prior to implantation, a connector block 690 is secured between the implant 660 and the humerus plate 750. The connector block 690 may be connected via screws (not shown) or the like. Upon connection, holes 754, 756, 758 and/or slot 760 in the humerus plate 750 are aligned with respective screw holes 676, 686 in the implant 660. The connector block 690 has a body 692 with a length equal to the distance between the intramedullary canal 108 and the external surface of the bone 102 such that upon positioning of the implant 660 in the canal 108, the humerus plate 750 extends along the surface of the bone 102. After the plate 750 and implant 660 have been inserted, at least one screw is inserted into one of the holes 754, 756 in the distal end of the plate 750 and into the aligned hole 676 in the implant 660 to lock the relative position of the plate 750 and implant 660. The connector block 690 may optionally be removed. The fracture is then reduced and screws are inserted in a normal manner.

The various intramedullary nail implants described herein may be made of bone, metal, plastic or other mostly rigid solids. The implants may provide the benefit of medial support to prevent collapse, ability to manipulate fragments using the device, and minimize the need for allograft, thereby decreasing biocompatibility issues. Other benefits may include minimizing the time spent shaping the fibula in the operating room, using a drill guide as a positioning arm for nail placement, ease of distal locking, and reducing negative affects to the rotator cuff. The various implants may also make revision easier to convert to shoulder arthroplasty. The various intramedullary nail implants also provide the benefit of either using or not using a lateral plate. When not using the lateral plate, the nail allows for a less invasive surgical approach, helps to avoid impingement, and may increase patient comfort. Additionally, at least some of the implants provide the flexibility to adjust implant position in the proximal/distal direction to facilitate fracture reduction.

With reference to FIGS. 44-47, a calcar blade implant 800 in accordance with an embodiment of the disclosure will be described. The implant 800 has a body 802 extending from a head 806 to a pointed tip 807. Referring to FIG. 45, the blade body 802 has a narrow structure, but may include ribs 804 extending from each side. The ribs 804 provide additional strength and help the implant 800 maintain trajectory as it is inserted. The blade body 802 has an arcuate configuration. The implant 800 will be inserted similar to a calcar screw and may be inserted as a standalone implant or optionally inserted through a plate 750 as illustrated. If inserted through a hole 758 in the plate body 752, the blade head 806 may be configured to lock to the plate body 752 to provide angular and rotational stability as well as preventing backout. Additionally or alternatively, the implant 800 may be utilized with an intramedullary nail and lock thereto.

The blade will behave similarly to a calcar screw, occupying the calcar region 106 of the proximal humerus 102 which has relatively high bone quality. Unlike the calcar screw, because of the arcuate configuration of the blade body 802, the tip 807 of the blade body 802 will be pointing proximally upon implantation. The blade body 802 may be made available in different angles/curvatures and lengths to address different anatomies and fracture needs. Further, there will be an optional means for adjustment of the implant 800 in varus/valgus and/or proximal/distal directions.

Figure 46:
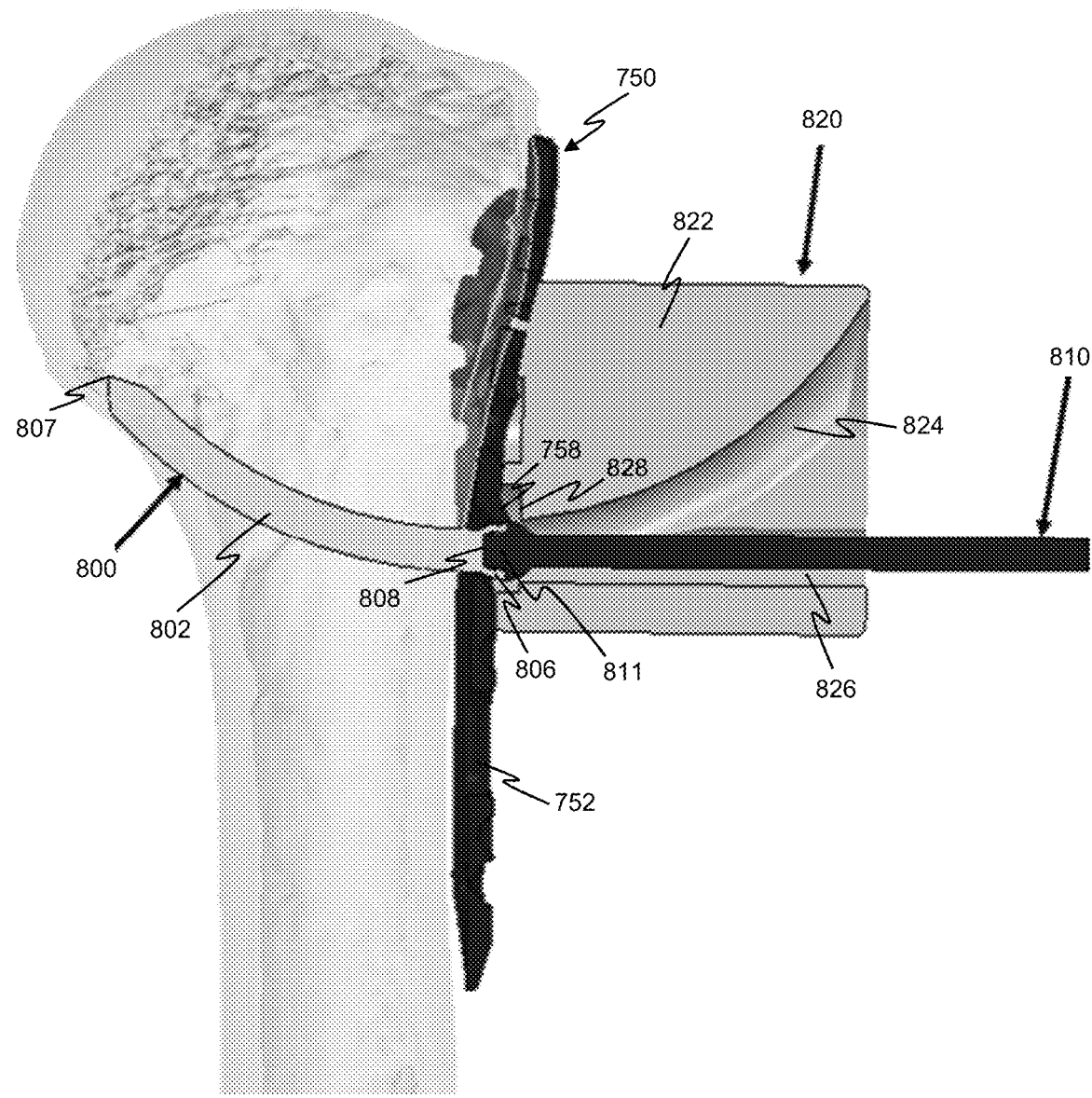
Figure 47:
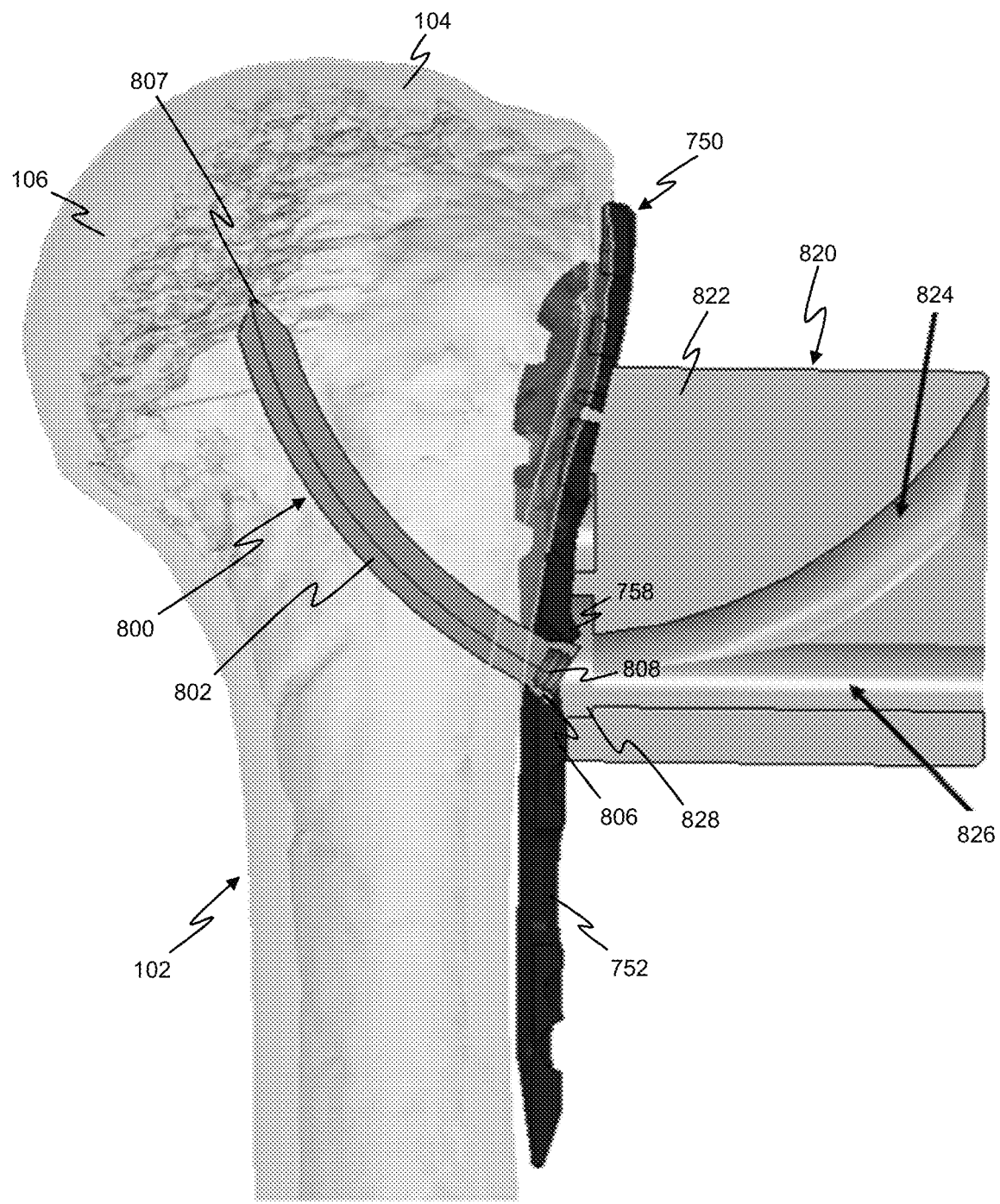

Referring to FIGS. 46 and 47, a method of implanting the calcar nail implant 800 in accordance with an embodiment of the disclosure is described. The illustrated method utilizes a guide block 820 through which the implant 800 passes to guide implantation. The guide block 820 has a body defining a curved passage 824 and a straight passage 826. The passages 824, 826 intersect at a common exit 828. The exit 828 is configured to be aligned with the desired point of entry of the implant 800. When utilized with a plate 750, the exit 828 is positionable about the screw hole 758.

The straight passage 826 allows for drilling of the lateral cortex. The surgeon can guide a drill bit through the passage 826 to drill a shallow hole to get through the cortical wall of high-quality bone to give the implant 800 a starting point. The curved passage 824 is configured to guide the head 806 of the implant 800 during implantation. The curved passage 824 preferably has a constant radius of curvature so that the implant 800 is guided along a continuous path.

The head 806 of the implant 800 has a recess 808 configured to receive a portion 811 of a tamp 810. The recess 808 and portion 811 may both be threaded for a threaded connection, however, other connection methods may be utilized, for example, press fit. The surgeon may impact the tamp with a mallet to impact the implant 800 into position. Again, the curved passage 824 guides the path of insertion of the curved body implant 800. The tamp 810 is removed after insertion.

With the curved configuration, the calcar nail implant 800 reduces the likelihood of lateral collapse of the humeral head by providing a broad surface normal to the direction of possible collapse. Additionally, the implant 800 anchors into to high quality calcar region utilizing an easy tamping procedure. The implant 800 can be utilized with a plate or a nail or may be utilized standalone. If utilized with a plate or nail, the implant 800 may be locked thereto.

Figure 48:
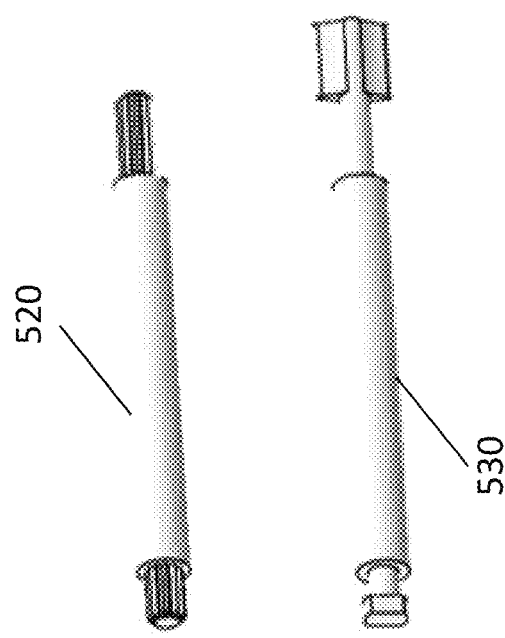
FIG. 48 illustrates an exemplary distal pinion gear and a distal alignment pin consistent with the principles of the present disclosure.

As previously described with regard to FIGS. 17-20, guide 500 may be used to reduce a fracture and thereafter guide 500, distal pinion gear pin 520, and distal alignment pin 530 are removed. Distal pinion gear pin 520 and distal alignment pin 530 are illustrated in FIG. 48. The use of these two pins requires drilling holes in the near cortex of the midshaft of the humerus. Following adjustment and locking of implant 110, as shown in FIG. 20, pins 520 and 530 are removed. This leaves two holes in the midshaft of the humerus. If the holes are not filled, the bone may refracture at the site of the holes.

Figure 49:
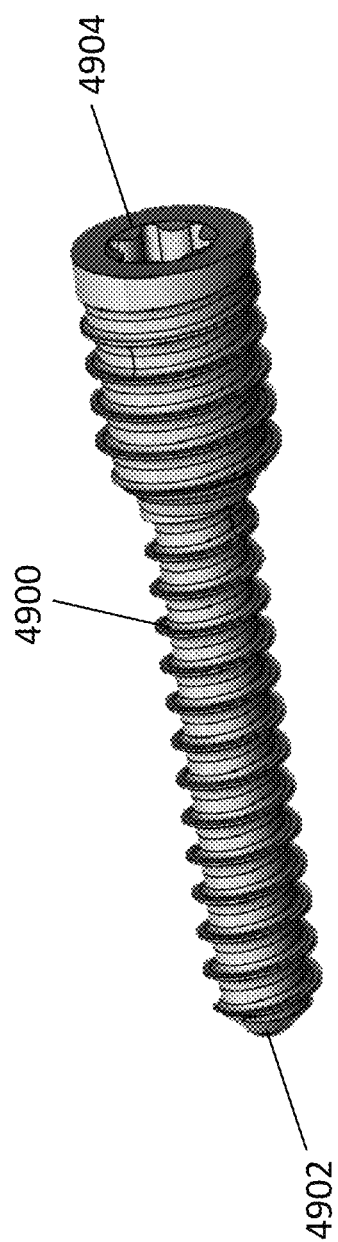
FIG. 49 illustrates an exemplary screw consistent with the principles of the present disclosure.
Figure 50B:
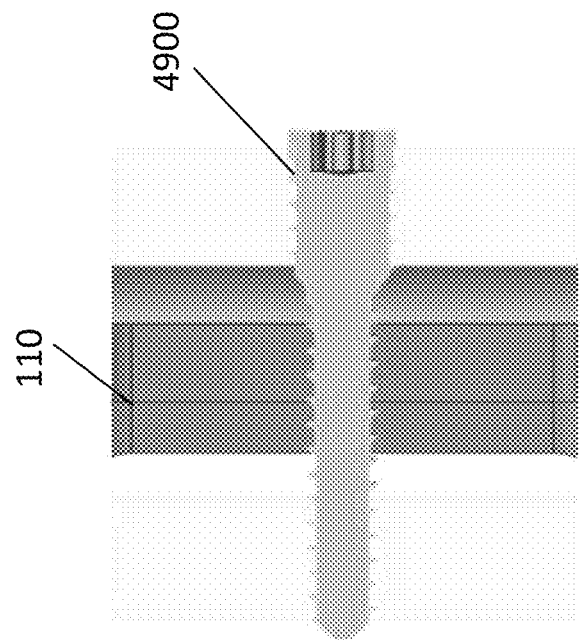
FIGS. 50A-50B illustrate an exemplary intramedullary nail and an exemplary screw consistent with the principles of the disclosure.
Figure 50A:
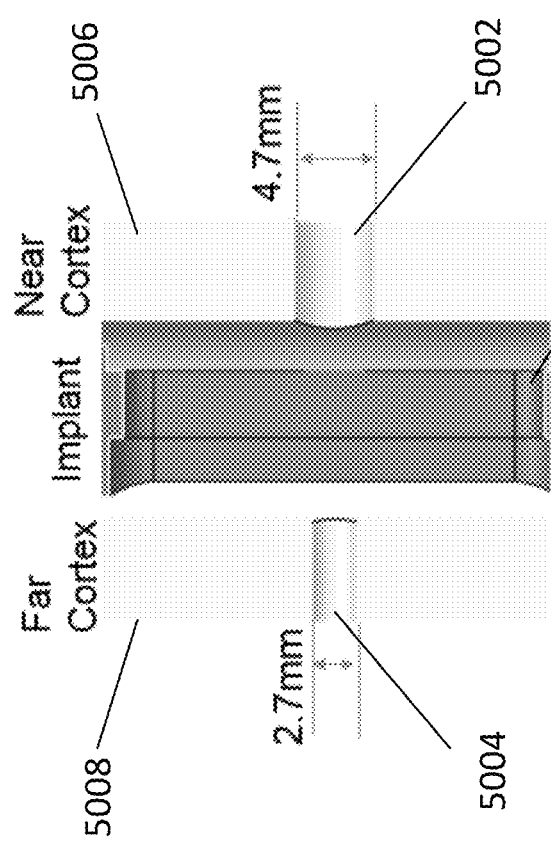
Figure 51:
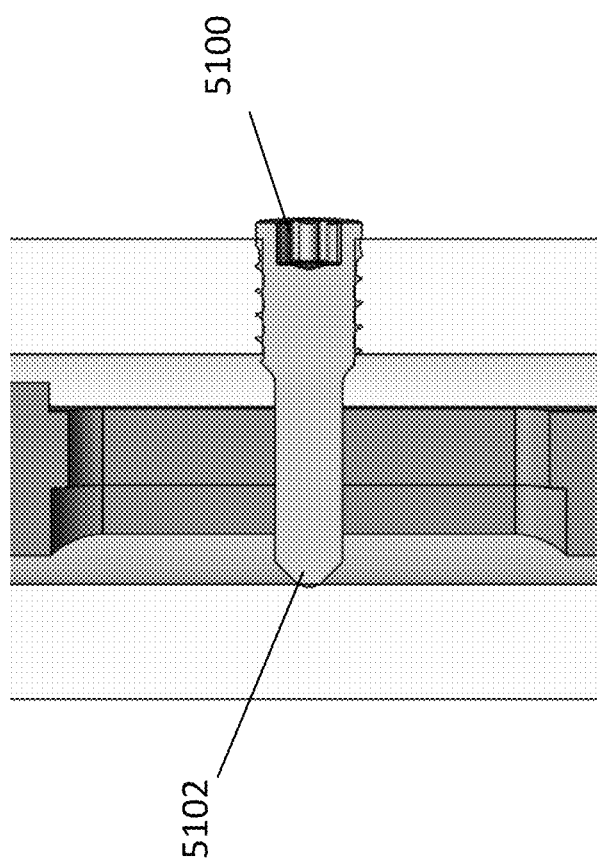
FIG. 51 illustrates an exemplary intramedullary nail and an exemplary screw consistent with the principles of the present disclosure.

FIGS. 49-51 illustrate exemplary screws that may be used to fill the hole created in the bone by pins 520 and 530. FIG. 49 illustrates a screw 4900 that may be used to fill those holes.

FIG. 50A illustrates holes 5002 and 5004 that have been drilled in a near cortex 5006 and a far cortex 5008 at the site of one of the holes created by the pins. Screw 4900 may be configured to pass through near cortex 5006 and implant 110 to achieve purchase in far cortex 5008, as shown in FIG. 50B. This seeks to provide more stability to the construct.

Screw 4900 may be configured to have a smaller diameter at a distal end 4902 relative to a proximal end 4904. In this embodiment, far cortex 5008 may be drilled to a smaller diameter to achieve fixation in far cortex 5008 and screw 4900 will be placed all the way through implant 110 to the bone. As an exemplary embodiment, FIGS. 50A-B illustrate a 2.7 mm hole at far cortex 5008 and a 4.7 mm hole at near cortex 5006. Screw 4900 would be correspondingly sized to fit within these holes, as shown in FIG. 50B.

As shown in FIG. 51, an exemplary screw 5100 may thread into the near cortex and an unthread stud 5102 may extend into implant 110 instead of being threaded at the distal end of the screw.

Without using either screw 4900 or screw 5100, two holes left unfilled in the bone in proximity to a fracture may cause an elevated stress concentration and lead to bone failure stemming from the holes acting as a defect. Placing a screw in these holes will reduce the concentration and allow surgeons to utilize the rack and pinion system of implant 110 and guide 500. Screw 4900 or screw 5100 may add rigidity to construct as shown in FIGS. 50B and 51.

These and other advantages of the present disclosure will be apparent to those skilled in the art from the foregoing specification. Accordingly, it will be recognized by those skilled in the art that changes or modifications may be made to the above-described embodiments without departing from the broad inventive concepts of the disclosure. It should therefore be understood that this disclosure is not limited to the particular embodiments described herein, but is intended to include all changes and modifications that are within the scope and spirit of the disclosure as defined in the claims.

What is claimed is:

1. A bone stabilization construct for positioning in a bone having a head and a shaft defining an intramedullary canal, the construct comprising:
    an intramedullary nail implant comprising:
        a distal portion including a shaft extending along a central axis and configured for positioning within the intramedullary canal, wherein the distal portion defines a slot, and the slot includes a rack extending along the central axis with a plurality of teeth extending into the slot; and
        a proximal portion extending proximally from the distal portion, the proximal portion defining a contact surface which extends at least in part medially of the central axis and which is configured to extend within the head of the bone;
    an aiming guide to position the intramedullary nail implant including a guide body having a proximal end and a distal end, wherein the guide body includes at least one slot, the at least one slot includes a rack extending along a longitudinal axis of the aiming guide with a plurality of teeth, wherein the rack of the guide body aligns with the rack of the intramedullary nail implant; and
    a screw, configured to fill a hole left from the aiming guide used to position the intramedullary nail implant, the screw comprising a distal end having a smaller diameter than a proximal end of the screw.

2. The bone stabilization construct according to claim 1, wherein the contact surface defines a curved surface.

3. The bone stabilization construct according to claim 1, wherein the proximal portion includes a solid structure with a plurality of screw holes defined therethrough.

4. The bone stabilization construct according to claim 1, wherein the proximal portion includes a thin-walled hollow structure.

5. The bone stabilization construct according to claim 1, wherein the rack of the intramedullary nail implant is configured for engagement with a pinion to adjust the position of the implant in a proximal or distal direction.

6. A bone stabilization construct for positioning in a bone having a head and a shaft defining an intramedullary canal, the construct comprising:
    an intramedullary nail implant comprising:
        a distal portion including a shaft extending along a central axis and configured for positioning within the intramedullary canal, wherein the distal portion defines a slot, and the slot includes a rack extending along the central axis with a plurality of teeth extending into the slot; and
        a proximal portion extending proximally from the distal portion, the proximal portion defining a contact surface which extends at least in part medially of the central axis and which is configured to extend within the head of the bone;
    an aiming guide to position the intramedullary nail implant including a guide body having a proximal end and a distal end, wherein the guide body includes at least one slot, the at least one slot includes a rack extending along a longitudinal axis of the aiming guide with a plurality of teeth, wherein the rack of the guide body aligns with the rack of the intramedullary nail implant; and
    a screw, configured to fill a hole left from the aiming guide used to position the intramedullary nail implant, the screw comprising a distal end having a smaller diameter than a proximal end of the screw, wherein the screw is threaded at the proximal end and has an unthreaded stud at the distal end.

7. The bone stabilization construct according to claim 6, wherein the contact surface defines a curved surface.

8. The bone stabilization construct according to claim 6, wherein the proximal portion includes a solid structure with a plurality of screw holes defined therethrough.

9. The bone stabilization construct according to claim 6, wherein the proximal portion includes a thin-walled hollow structure.

* * * * *